United States Patent
Pertijs et al.

(10) Patent No.: US 9,060,692 B2
(45) Date of Patent: Jun. 23, 2015

(54) TEMPERATURE SENSOR FOR A LEADLESS CARDIAC PACEMAKER

(71) Applicant: Nanostim, Inc., Sunnyvale, CA (US)

(72) Inventors: Michiel Pertijs, Delft (NL); Kenneth J. Carroll, Los Altos, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 117 days.

(21) Appl. No.: 13/901,414

(22) Filed: May 23, 2013

(65) Prior Publication Data
US 2013/0261497 A1    Oct. 3, 2013

Related U.S. Application Data

(63) Continuation-in-part of application No. 13/272,092, filed on Oct. 12, 2011, now Pat. No. 8,543,205.

(60) Provisional application No. 61/392,382, filed on Oct. 12, 2010, provisional application No. 61/650,819, filed on May 23, 2012.

(51) Int. Cl.
*A61N 1/365* (2006.01)
*A61B 5/01* (2006.01)
*A61B 5/00* (2006.01)
*A61N 1/375* (2006.01)

(52) U.S. Cl.
CPC .............. *A61B 5/01* (2013.01); *A61N 1/3655* (2013.01); *A61B 5/686* (2013.01); *A61N 1/36514* (2013.01); *A61N 1/3756* (2013.01)

(58) Field of Classification Search
CPC ................................ A61B 5/01; A61N 1/3655
USPC ............................................... 607/21, 17, 18
See application file for complete search history.

(56) References Cited

U.S. PATENT DOCUMENTS

| | | |
|---|---|---|
| 3,199,508 A | 8/1965 | Roth |
| 3,212,496 A | 10/1965 | Preston |

(Continued)

FOREIGN PATENT DOCUMENTS

| | | |
|---|---|---|
| EP | 1741465 A1 | 1/2007 |
| JP | H04-506167 A | 10/1992 |

(Continued)

OTHER PUBLICATIONS

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. 7,630,767).

(Continued)

*Primary Examiner* — George Evanisko
(74) *Attorney, Agent, or Firm* — Theresa A. Raymer

(57) ABSTRACT

A leadless cardiac pacemaker comprises a hermetic housing, a power source disposed in the housing, at least two electrodes supported by the housing, a semiconductor temperature sensor disposed in the housing, and a controller disposed in the housing and configured to deliver energy from the power source to the electrodes to stimulate the heart based upon temperature information from the temperature sensor. In some embodiments, the sensor can be configured to sense temperature information within a predetermined range of less than 20 degrees C. The temperature sensor can be disposed in the housing but not bonded to the housing.

10 Claims, 19 Drawing Sheets

(56) References Cited

U.S. PATENT DOCUMENTS

| | | |
|---|---|---|
| 3,218,638 A | 11/1965 | Honig |
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |
| 3,943,926 A | 3/1976 | Barragan |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,458,692 A | 7/1984 | Simson |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,858,610 A | 8/1989 | Callaghan et al. |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A | 1/1991 | Funke |
| 4,995,390 A | 2/1991 | Cook et al. |
| 5,010,887 A | 4/1991 | Thornander |
| 5,012,806 A | 5/1991 | De Bellis |
| 5,014,701 A | 5/1991 | Pless et al. |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A | 11/1993 | Bens |
| 5,267,150 A | 11/1993 | Wilkinson |
| 5,282,841 A | 2/1994 | Szyszkowski |
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,331,966 A | 7/1994 | Bennett et al. |
| 5,333,095 A | 7/1994 | Stevenson et al. |
| 5,336,244 A | 8/1994 | Weijand |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |
| 5,411,532 A | 5/1995 | Mortazavi |
| 5,411,535 A | 5/1995 | Fujii |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |

(56) References Cited

U.S. PATENT DOCUMENTS

| | | |
|---|---|---|
| 5,446,447 A | 8/1995 | Carney et al. |
| 5,456,261 A | 10/1995 | Luczyk |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,531,781 A | 7/1996 | Alferness et al. |
| 5,531,783 A | 7/1996 | Giele et al. |
| 5,539,775 A | 7/1996 | Tuttle et al. |
| 5,549,654 A | 8/1996 | Powell |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |
| 5,571,143 A | 11/1996 | Hoegnelid et al. |
| 5,730,143 A | 3/1998 | Schwarzberg |
| 5,735,880 A | 4/1998 | Prutchi et al. |
| 5,738,102 A | 4/1998 | Lemelson |
| 5,740,811 A | 4/1998 | Hedberg et al. |
| 5,741,314 A | 4/1998 | Daly et al. |
| 5,766,231 A | 6/1998 | Erickson et al. |
| 5,792,205 A | 8/1998 | Alt et al. |
| 5,810,735 A | 9/1998 | Halperin et al. |
| 5,814,076 A | 9/1998 | Brownlee |
| 5,814,087 A | 9/1998 | Renirie |
| 5,814,089 A | 9/1998 | Stokes et al. |
| 5,824,016 A | 10/1998 | Ekwall |
| 5,871,451 A | 2/1999 | Unger et al. |
| 5,876,353 A | 3/1999 | Riff |
| 5,876,425 A | 3/1999 | Gord et al. |
| 5,891,178 A | 4/1999 | Mann et al. |
| 5,899,928 A | 5/1999 | Sholder et al. |
| 5,935,079 A | 8/1999 | Swanson et al. |
| 5,954,761 A | 9/1999 | Machek et al. |
| 5,957,861 A | 9/1999 | Combs et al. |
| 5,984,861 A | 11/1999 | Crowley |
| 5,987,352 A | 11/1999 | Klein et al. |
| 5,995,876 A | 11/1999 | Kruse et al. |
| 5,999,857 A | 12/1999 | Weijand et al. |
| 6,002,969 A | 12/1999 | Machek et al. |
| 6,004,269 A | 12/1999 | Crowley et al. |
| 6,061,596 A | 5/2000 | Richmond et al. |
| 6,076,016 A | 6/2000 | Feierbach |
| 6,080,187 A | 6/2000 | Alt et al. |
| 6,093,146 A | 7/2000 | Filangeri |
| 6,096,065 A | 8/2000 | Crowley |
| 6,102,874 A | 8/2000 | Stone et al. |
| 6,112,116 A | 8/2000 | Fischell et al. |
| 6,115,628 A | 9/2000 | Stadler et al. |
| 6,115,630 A | 9/2000 | Stadler et al. |
| 6,115,636 A | 9/2000 | Ryan |
| 6,119,031 A | 9/2000 | Crowley |
| 6,125,290 A | 9/2000 | Miesel |
| 6,125,291 A | 9/2000 | Miesel et al. |
| 6,128,526 A | 10/2000 | Stadler et al. |
| 6,129,751 A | 10/2000 | Lucchesi et al. |
| 6,132,390 A | 10/2000 | Cookston et al. |
| 6,132,456 A | 10/2000 | Sommer et al. |
| 6,134,459 A | 10/2000 | Roberts et al. |
| 6,134,470 A | 10/2000 | Hartlaub |
| 6,139,510 A | 10/2000 | Palermo |
| 6,141,584 A | 10/2000 | Rockwell et al. |
| 6,141,588 A | 10/2000 | Cox et al. |
| 6,141,592 A | 10/2000 | Pauly |
| 6,144,866 A | 11/2000 | Miesel et al. |
| 6,148,230 A | 11/2000 | KenKnight |
| 6,152,882 A | 11/2000 | Prutchi |
| 6,163,723 A | 12/2000 | Roberts et al. |
| 6,164,284 A | 12/2000 | Schulman et al. |
| 6,167,310 A | 12/2000 | Grevious |
| 6,178,349 B1 | 1/2001 | Kieval |
| 6,178,356 B1 | 1/2001 | Chastain et al. |
| 6,185,443 B1 | 2/2001 | Crowley |
| 6,185,452 B1 | 2/2001 | Schulman et al. |
| 6,185,464 B1 | 2/2001 | Bonner et al. |
| 6,188,932 B1 | 2/2001 | Lindegren |
| 6,190,324 B1 | 2/2001 | Kieval et al. |
| 6,198,952 B1 | 3/2001 | Miesel |
| 6,201,993 B1 | 3/2001 | Kruse et al. |
| 6,208,894 B1 | 3/2001 | Schulman et al. |
| 6,208,900 B1 | 3/2001 | Ecker et al. |
| 6,223,081 B1 | 4/2001 | Kerver |
| 6,230,059 B1 | 5/2001 | Duffin |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,266,564 B1 | 7/2001 | Hill et al. |
| 6,272,379 B1 | 8/2001 | Fischell et al. |
| 6,280,409 B1 | 8/2001 | Stone et al. |
| 6,289,229 B1 | 9/2001 | Crowley |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,498,951 B1 | 12/2002 | Larson et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |

(56) References Cited

U.S. PATENT DOCUMENTS

| | | |
|---|---|---|
| 6,522,928 B2 | 2/2003 | Whitehurst et al. |
| 6,539,257 B1 | 3/2003 | KenKnight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 | 4/2004 | Thompson et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 | 2/2005 | Bardy et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 | 4/2006 | Goetz et al. |
| 7,027,876 B2 | 4/2006 | Casavant et al. |
| 7,146,222 B2 | 12/2006 | Boling |
| 7,146,225 B2 | 12/2006 | Guenst et al. |
| 7,164,950 B2 | 1/2007 | Kroll et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland |
| 7,277,754 B2 | 10/2007 | McCabe et al. |
| 7,289,853 B1 | 10/2007 | Campbell et al. |
| 7,363,090 B2 | 4/2008 | Halperin et al. |
| 7,558,631 B2 | 7/2009 | Cowan et al. |
| 7,565,195 B1 | 7/2009 | Kroll et al. |
| 7,616,991 B2 | 11/2009 | Mann et al. |
| 7,630,767 B1 | 12/2009 | Poore et al. |
| 7,634,313 B1 | 12/2009 | Kroll et al. |
| 7,848,823 B2 | 12/2010 | Drasler et al. |
| 7,937,148 B2 | 5/2011 | Jacobson |
| 7,945,333 B2 | 5/2011 | Jacobson |
| 8,010,209 B2 | 8/2011 | Jacobson |
| 8,295,939 B2 | 10/2012 | Jacobson |
| 8,352,025 B2 | 1/2013 | Jacobson |
| 8,457,742 B2 | 6/2013 | Jacobson |
| 8,527,068 B2 | 9/2013 | Ostroff |
| 8,543,205 B2 * | 9/2013 | Ostroff ............ 607/21 |
| 2001/0031999 A1 | 10/2001 | Carter et al. |
| 2002/0032467 A1 | 3/2002 | Shemer et al. |
| 2002/0077686 A1 | 6/2002 | Westlund et al. |
| 2002/0116028 A1 | 8/2002 | Greatbatch et al. |
| 2002/0147488 A1 | 10/2002 | Doan et al. |
| 2003/0141995 A1 | 7/2003 | Lin |
| 2003/0158584 A1 | 8/2003 | Cates et al. |
| 2003/0163184 A1 | 8/2003 | Scheiner et al. |
| 2003/0199941 A1 | 10/2003 | Nielsen et al. |
| 2004/0011366 A1 | 1/2004 | Schulman et al. |
| 2004/0059392 A1 | 3/2004 | Parramon et al. |
| 2004/0116939 A1 | 6/2004 | Goode |
| 2004/0133242 A1 | 7/2004 | Chapman et al. |
| 2004/0143262 A1 | 7/2004 | Visram et al. |
| 2004/0147973 A1 | 7/2004 | Hauser |
| 2004/0167587 A1 | 8/2004 | Thompson |
| 2004/0172116 A1 | 9/2004 | Seifert et al. |
| 2004/0193223 A1 | 9/2004 | Kramer et al. |
| 2004/0249417 A1 | 12/2004 | Ransbury et al. |
| 2004/0260349 A1 | 12/2004 | Stroebel |
| 2005/0038474 A1 | 2/2005 | Wool |

(56) References Cited

U.S. PATENT DOCUMENTS

| | | |
|---|---|---|
| 2005/0038491 A1 | 2/2005 | Haack |
| 2005/0043765 A1 | 2/2005 | Williams et al. |
| 2005/0075682 A1 | 4/2005 | Schulman et al. |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll |
| 2006/0108335 A1 | 5/2006 | Zhao et al. |
| 2006/0121475 A1 | 6/2006 | Davids et al. |
| 2006/0135999 A1 | 6/2006 | Bodner et al. |
| 2006/0136004 A1 | 6/2006 | Cowan et al. |
| 2006/0161222 A1 | 7/2006 | Haubrich et al. |
| 2006/0241705 A1 | 10/2006 | Neumann et al. |
| 2006/0247750 A1 | 11/2006 | Seifert et al. |
| 2006/0282150 A1 | 12/2006 | Olson et al. |
| 2007/0016263 A1 | 1/2007 | Armstrong et al. |
| 2007/0043414 A1 | 2/2007 | Fifer et al. |
| 2007/0055184 A1 | 3/2007 | Echt et al. |
| 2007/0088396 A1 | 4/2007 | Jacobson |
| 2007/0088397 A1 | 4/2007 | Jacobson |
| 2007/0123923 A1 | 5/2007 | Lindstrom et al. |
| 2007/0142709 A1 | 6/2007 | Martone et al. |
| 2007/0179552 A1 | 8/2007 | Dennis et al. |
| 2007/0270675 A1 | 11/2007 | Kane et al. |
| 2007/0276004 A1 | 11/2007 | Hirsch et al. |
| 2007/0276444 A1 | 11/2007 | Gelbart et al. |
| 2007/0293904 A1 | 12/2007 | Gelbart et al. |
| 2008/0004535 A1 | 1/2008 | Smits |
| 2008/0021532 A1 | 1/2008 | Kveen et al. |
| 2008/0039738 A1 | 2/2008 | Dinsmoor et al. |
| 2008/0086168 A1 | 4/2008 | Cahill |
| 2008/0091255 A1 | 4/2008 | Caparso et al. |
| 2008/0119911 A1 | 5/2008 | Rosero |
| 2008/0243218 A1 | 10/2008 | Bottomley et al. |
| 2008/0269591 A1 | 10/2008 | Halperin et al. |
| 2009/0018599 A1 | 1/2009 | Hastings et al. |
| 2009/0082827 A1 | 3/2009 | Kveen et al. |
| 2009/0082828 A1 | 3/2009 | Ostroff |
| 2009/0149902 A1 | 6/2009 | Kumar et al. |
| 2009/0171408 A1 | 7/2009 | Solem |
| 2010/0069983 A1 | 3/2010 | Peacock et al. |
| 2010/0211149 A1 | 8/2010 | Morgan et al. |
| 2010/0249828 A1 | 9/2010 | Mavani et al. |
| 2010/0292541 A1 | 11/2010 | Hashiba et al. |
| 2010/0305653 A1 | 12/2010 | Lund et al. |
| 2010/0305656 A1 | 12/2010 | Imran et al. |
| 2010/0312332 A1 | 12/2010 | Forster et al. |
| 2011/0004117 A1 | 1/2011 | Neville et al. |
| 2011/0071586 A1 | 3/2011 | Jacobson |
| 2011/0077708 A1 | 3/2011 | Ostroff |
| 2011/0208260 A1 | 8/2011 | Jacobson |
| 2011/0282423 A1 | 11/2011 | Jacobson |
| 2012/0089198 A1 | 4/2012 | Ostroff |
| 2012/0095539 A1 | 4/2012 | Khairkhahan et al. |
| 2012/0109236 A1 | 5/2012 | Jacobson et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0197373 A1 | 8/2012 | Khairkhahan et al. |
| 2012/0245665 A1 | 9/2012 | Friedman et al. |
| 2013/0041422 A1 | 2/2013 | Jacobson |
| 2013/0103109 A1 | 4/2013 | Jacobson |
| 2013/0123875 A1 | 5/2013 | Varady et al. |

FOREIGN PATENT DOCUMENTS

| | | |
|---|---|---|
| JP | 05-245215 | 9/1993 |
| JP | 06/507096 | 3/2006 |
| JP | 06/516449 | 7/2006 |
| WO | WO93/12714 A1 | 7/1993 |
| WO | WO02/34333 A2 | 5/2002 |
| WO | WO2004/012811 | 2/2004 |
| WO | WO 2006/065394 A1 | 6/2006 |
| WO | WO 2007/047681 A2 | 4/2007 |
| WO | WO 2007/059386 A2 | 5/2007 |
| WO | WO 2008/058265 A2 | 5/2008 |
| WO | WO2010/088116 A1 | 8/2010 |

OTHER PUBLICATIONS

Beeby et al.; Micromachined silicon generator for harvesting power from vibrations; (Proceedings) PowerMEMS 2004; Kyoto, Japan; pp. 104-107; Nov. 28-30, 2004.

Bordacher et al.; Impact and prevention of far-field sensing in fallback mode switches; PACE; vol. 26 (pt. II); pp. 206-209; Jan. 2003.

Brandt et al.; Far-field QRS complex sensing: prevalence and timing with bipolar atrial leads; PACE; vol. 23; pp. 315-320; Mar. 2000.

Brown, Eric S.; The atomic battery; Technology Review: Published by MIT; 4 pgs.; Jun. 16, 2005.

Irnich et al.; Do we need pacemakers resistant to magnetic resonance imaging; Europace; vol. 7; pp. 353-365; Feb. 2005.

Irnich; Electronic security systems and active implantable medical devices; Journal of PACE; vol. 25; No. 8; pp. 1235-1258; Aug. 2002.

Luechinger et al.; Force and torque effects of a 1.5-tesla MRI scanner of cardiac pacemakers and ICDs; Journal of PACE; vol. 24; No. 2; pp. 199-205; Feb. 2001.

Luechinger et al.; In vivo heating of pacemaker leads during magnetic resonance imaging; European Heart Journal; vol. 26; pp. 376-383; Feb. 2005.

Lüchinger ; Safety aspects of cardiac pacemakers in magnetic resonance imaging; Dissertation submitted to the Swiss Federal Institute of Technology Zurich; 137 pages; (year of publication is sufficiently earlier than the effective U.S. filing date and any foreign priority date) 2002.

Nyenhuis et al.; MRI and Implanted Medical Devices: Basic Interactions with an emphasis on heating; vol. 5; No. 3; pp. 467-480; Sep. 2005.

Shellock et al.; Cardiac pacemaker: in vitro assessment at 1.5 T; Am Heart J; vol. 151; No. 2; pp. 436-443; Feb. 2006.

Jacobson, P.; U.S. Appl. No. 13/866,803 entitled "Leadless cardiac pacemaker system for usage in combination with an implantable cardioverter-defribrillator," filed Apr. 19, 2013.

Ostroff et al.; U.S. Appl. No. 13/910,896 entitled "Leadless Pacemaker with Multiple Electrodes," filed Jun. 5, 2013.

Ostroff, Alan; U.S. Appl. No. 13/915,560 entitled "MRI Compatible Leadless Cardiac Pacemaker," filed Jun. 11, 2013.

Carroll et al.; U.S. Appl. No. 13/956,946 entitled "Biostimulator Circuit with Flying Cell," filed Aug. 1, 2013.

Ostroff, Alan; U.S. Appl. No. 13/967,180 entitled "Leadless Cardiac Pacemaker with Secondary Fixation Capability" filed Aug. 14, 2013.

* cited by examiner

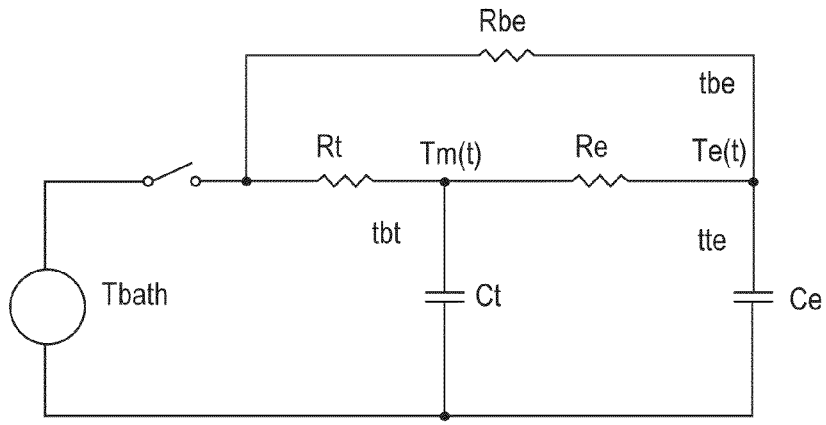

Let:

t = time since immersion in bath
   Th = bath temperature
   Tc = start temperature
   Tm(t) = thermistor temperature, measured
   Tt(t) = thermistor temperature, simulated
   Te(t) = adhesive + silicone temperature, simulated
   $\tau bt$ = bath-to-thermistor time constant
   $\tau be$ = bath-to-adhesive + silicone time constant
   $\tau te$ = thermistor-to-adhesive + silicone time constant Then:

$$\frac{Th - Te(t)}{Th - Tc} = e^{\frac{t}{\tau be}}$$

$$Te(t) = Th - (Th - Tc) \cdot e^{\frac{t}{\tau be}}$$

$$Tt(t2) - Tt(t1) = \left[ \frac{Th - Tt(t1)}{\tau bt} - \frac{Tt(t1) - Te(t1)}{\tau te} \right] \cdot (t2 - t1)$$

FIG. 6

Time constants derived from Example 1:

| symbol | parameter | value | units |
|---|---|---|---|
| τbt | Bath-to-thermistor time constant | 4.3 | seconds |
| τbe | Bath-to-adhesive + silicone time constant | 9.7 | seconds |
| τte | Thermistor-to-adhesive + silicone time constant | 1.5 | seconds |

Time constants derived from Example 2:

| symbol | parameter | value | units |
|---|---|---|---|
| τbt | Bath-to-thermistor time constant | 3.0 | seconds |
| τbe | Bath-to-adhesive time constant | 10.0 | seconds |
| τte | Thermistor-to-adhesive time constant | 6.0 | seconds |

Time constants derived from Example 3:

| symbol | parameter | value | units |
|---|---|---|---|
| τbt | Bath-to-thermistor time constant | 4.0 | seconds |
| τbe | Bath-to-adhesive time constant | 9.7 | seconds |
| τte | Thermistor-to-adhesive time constant | 1.5 | seconds |

Time constants derived from Example 4:

| symbol | parameter | value | units |
|---|---|---|---|
| τbt | Bath-to-thermistor time constant | 3.4 | seconds |
| τbe | Bath-to-adhesive time constant | 3.4 | seconds |
| τte | Thermistor-to-adhesive time constant | ∞ | seconds |

Time constants derived from Example 5:

| symbol | parameter | value | units |
|---|---|---|---|
| τbt | Bath-to-thermistor time constant | 5.5 | seconds |
| τbe | Bath-to-air time constant | 16.0 | seconds |
| τte | Thermistor-to-air time constant | 3.9 | seconds |

Time constants derived from Example 6:

| symbol | parameter | value | units |
|---|---|---|---|
| τbt | Bath-to-thermistor time constant | 11.8 | seconds |
| τbe | Bath-to-wire time constant | 23.3 | seconds |
| τte | Thermistor-to-wire time constant | 3.9 | seconds |

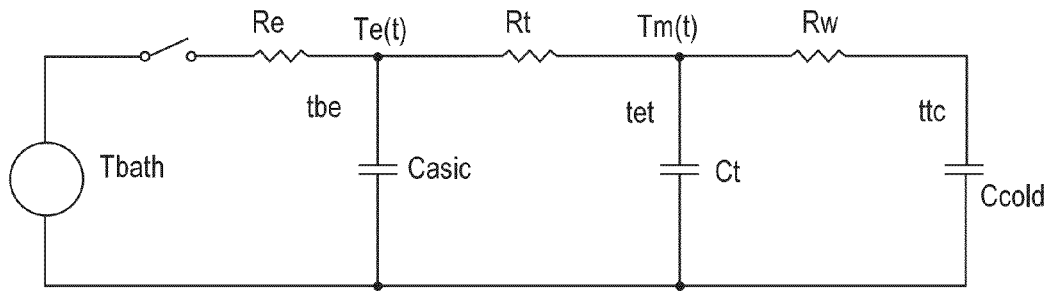

Let:

t = time since immersion in bath
Th = bath temperature
Tc = start temperature
Tm(t) = thermistor temperature, measured
Tt(t) = thermistor temperature, simulated
Te(t) = ASIC-temperature, simulated
τet = ASIC-to-thermistor time constant
τbe = bath-to-ASIC time constant
τtc = thermistor-to-wire time constant Then:

$$\frac{Th - Te(t)}{Th - Tc} = e^{\frac{t}{tbe}}$$

$$Te(t) = Th - (Th - Tc) \cdot e^{\frac{t}{tbe}}$$

$$Tt(t2) - Tt(t1) = \left[\frac{Te(t1) - Tt(t1)}{\tau et} - \frac{(Tt(t1) - Tc)}{\tau tc}\right] \cdot (t2 - t1)$$

FIG. 13

Time constants derived from Example 7:

| symbol | parameter | value | units |
|---|---|---|---|
| $\tau_{et}$ | ASIC-to-thermistor time constant | 1.4 | seconds |
| $\tau_{be}$ | Bath-to-ASIC time constant | 12.9 | seconds |
| $\tau_{tc}$ | Thermistor-to-wire time constant | 100 | seconds |

TEMPERATURE SENSOR FOR A LEADLESS CARDIAC PACEMAKER

CROSS REFERENCE TO RELATED APPLICATIONS

This application is a continuation-in-part of U.S. patent application Ser. No. 13/272,092, filed Oct. 12, 2011, entitled "Temperature Sensor for a Leadless Cardiac Pacemaker", now U.S. Pat. No. 8,543,205, which application claims the benefit of U.S. Provisional Patent Application No. 61/392,382, filed Oct. 12, 2010. This application also claims the benefit of U.S. Provisional Patent Application No. 61/650,819, filed May 23, 2012, titled "Temperature Sensor for a Leadless Cardiac Pacemaker", the contents of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Cardiac pacing by an artificial pacemaker provides an electrical stimulation of the heart when the heart's own natural pacemaker and/or conduction system fails to provide synchronized atrial and ventricular contractions at rates and intervals sufficient for a patient's health. Such antibradycardial pacing provides relief from symptoms and even life support for hundreds of thousands of patients.

The rate of stimulation provided by a pacemaker may need to be adjusted to match the level of the patient's physical activity. Prior rate responsive pacemakers have relied on, among other parameters, central venous temperature to indicate the need to adjust stimulation rates up or down. Prior devices often used temperature sensors connected to the pacemaker body by a lead extending from the pacemaker body's location outside of the heart to a temperature sensor located within the patient's heart. These devices typically include temperature sensors that are disposed directly in the blood stream of the patient.

SUMMARY OF THE DISCLOSURE

A semiconductor temperature sensor is provided, comprising at least one bipolar transistor configured to generate a complimentary-to-absolute-temperature (CTAT) signal derived from a base-emitter voltage of the at least one bipolar transistor, first and second proportional-to-absolute-temperature (PTAT) signals derived from the at least one bipolar transistor, the first PTAT signal being equal to the CTAT signal at a first temperature, the second PTAT signal being equal to the CTAT signal at a second temperature, and an analog-to-digital converter (ADC) configured to covert the CTAT signal and the first and second PTAT signals into a digital temperature output signal, and a controller configured to scale the digital temperature output signal to represent a preferred temperature scale.

In some embodiments, the preferred temperature scale comprises a Celsius scale. In other embodiments, the preferred temperature scale comprises a Fahrenheit scale. In another embodiment, the preferred temperature scale comprises a Kelvin scale.

In some embodiments, the first and second PTAT signals are derived from a single bipolar transistor to which first and second bias currents are successively applied.

In one embodiment, the at least one bipolar transistor comprises a first bipolar transistor and a second bipolar transistor, wherein the first and second PTAT signals are derived from a difference in base-emitter voltages between the first and second bipolar transistors.

In another embodiment, the ADC comprises a charge-balancing ADC. In some embodiments, the charge-balancing ADC is configured to balance a charge accumulated proportional to the CTAT signal by negative feedback with a charge proportional to the first or second PTAT signals. In another embodiment, an intermediate signal in the charge-balancing ADC is configured to determine which of the first or second PTAT signals is used in the negative feedback path, such that a charge provided by the negative feedback path equals a charge provided by the CTAT signal. In another embodiment, an average value of the intermediate signal is equal to a relative value of the CTAT signal with respect to the first and second PTAT signals.

A method of measuring temperature with a semiconductor temperature sensor is also provided, comprising deriving a complimentary-to-absolute-temperature (CTAT) signal from a base-emitter voltage of at least one bipolar transistor, deriving first and second proportional-to-absolute-temperature (PTAT) signals from the at least one bipolar transistor, wherein the first PTAT signal is approximately equal to the CTAT signal at a first temperature, wherein the second PTAT signal is approximately equal to the CTAT signal at a second temperature, converting the CTAT signal and the first and second PTAT signals into a digital temperature output signal with an analog-to-digital converter (ADC), and scaling the digital temperature output signal to represent a preferred temperature scale.

In some embodiments, the method further comprises calibrating the semiconductor temperature sensor at a first temperature to establish an initial temperature error.

In another embodiment, the method further comprises correcting a bias current used to generate the CTAT signal to bring an initial temperature error within range of the ADC.

A leadless cardiac pacemaker is provided, comprising a hermetic housing configured to be implanted in a chamber of a human heart, a power source disposed in the housing, at least two electrodes supported by the housing, a semiconductor temperature sensor disposed in the housing, comprising, at least one bipolar transistor configured to generate a complimentary-to-absolute-temperature (CTAT) signal derived from a base-emitter voltage of at least one bipolar transistor, and first and second proportional-to-absolute-temperature (PTAT) signals derived from the at least one bipolar transistor, the first PTAT signal being equal to the CTAT signal at a first temperature, the second PTAT signal being equal to the CTAT signal at a second temperature, an analog-to-digital converter (ADC) configured to covert the CTAT signal and the first and second PTAT signals into a digital temperature output signal, a controller disposed in the housing and configured to deliver energy from the power source to the electrodes to stimulate the heart based on the digital temperature output signal from the semiconductor temperature sensor.

In some embodiments, the pacemaker further comprises a fixation helix adapted to attach the hermetic housing to the heart.

In another embodiment, the semiconductor temperature sensor is not bonded to the housing.

A leadless cardiac pacemaker is provided, comprising a hermetic housing configured to be implanted in a chamber of a human heart, a switched-bias power source disposed in the housing, at least two electrodes supported by the housing, a semiconductor temperature sensor comprising at least one bipolar transistor configured to generate a complimentary-to-absolute-temperature (CTAT) signal derived from a base-emitter voltage of at least one bipolar transistor, and first and second proportional-to-absolute-temperature (PTAT) signals derived from the at least one bipolar transistor, the first PTAT signal being generated by operating the at least one bipolar transistor at a first pair of current densities, the second PTAT signal being generated by operating the at least one bipolar transistor at a second pair of current densities, wherein a first ratio of the first pair of current densities differs from a second ratio of the second pair of current densities, an analog-to-digital converter (ADC) configured to covert the CTAT signal and the first and second PTAT signals into a digital temperature output signal, and a controller disposed in the housing and configured to deliver energy from the power source to the electrodes to stimulate the heart based upon the digital temperature output signal from the semiconductor temperature sensor.

In some embodiments, the pacemaker further comprises a fixation helix adapted to attach the hermetic housing to the heart.

In another embodiment, the semiconductor temperature sensor is not bonded to the housing.

A leadless cardiac pacemaker is provided, comprising a hermetic housing configured to be disposed in a chamber of a human heart, a power source disposed in the housing, at least two electrodes supported by the housing, a semiconductor temperature sensor disposed in the housing, the semiconductor temperature sensor being configured to sense temperature information within a predetermined range of less than 20 degrees C., and a controller disposed in the housing and configured to deliver energy from the power source to the electrodes to stimulate the heart based upon temperature information from the temperature sensor.

In one embodiment, the semiconductor temperature sensor is configured to sense temperature information within a predetermined range of less than 10 degrees C.

In another embodiment, the semiconductor temperature sensor is configured to sense temperature information within a predetermined range of 36 to 42 degrees C.

In an additional embodiment, the controller comprises an ASIC and the semiconductor temperature sensor is incorporated into the ASIC.

In some embodiments, the semiconductor temperature sensor is configured to sense the temperature of blood surrounding the leadless cardiac pacemaker.

In one embodiment, the semiconductor temperature sensor is not bonded to the housing.

In some embodiments, the semiconductor temperature sensor includes a low-resolution analog-to-digital converter adapted to consume less than 100 nA of current at greater than 0.1 temperature samples per second.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 6 is one embodiment of a thermal circuit for use in a leadless cardiac pacemaker.

FIG. 13 is another embodiment of a thermal circuit for use in a leadless cardiac pacemaker.

DETAILED DESCRIPTION

This disclosure relates to a rate responsive leadless cardiac pacemaker or other leadless biostimulator. The leadless biostimulator can be implanted within a chamber of the patient's heart. The rate responsive leadless biostimulator can employ a temperature sensor, such as a digital output sensor having bipolar transistors, that is supported by the biostimulator housing. The leadless biostimulator of this disclosure can use the measured temperature to adjust the rate of its electrical stimulation signals.

In some embodiments, the leadless biostimulator may include a hermetic housing disposed in a chamber of a human heart, a battery disposed in the housing, at least two electrodes supported by the housing, a temperature sensor supported by the housing and a controller disposed in the housing. The controller can be adapted to sense intracardiac information using the two electrodes and to deliver stimulation energy from the battery to the electrode using temperature information from the temperature sensor. The temperature sensor may be supported by the leadless biostimulator housing in any manner consistent with the thermal time constant requirements of the system. The temperature sensor may be a thermistor or a semiconductor temperature sensor incorporated into the controller.

In order to use central venous temperature as the metabolic parameter for a rate response algorithm, the leadless biostimulator must be able to sense and respond to changes in central venous temperatures within a clinically significant period of time, such as less than 30 seconds. Since the leadless biostimulator will be disposed in contact with the patient's blood within the patient's heart, the biostimulator design must provide a heat conduction path from the blood to the temperature sensing element whose time constant is sufficiently small to allow the sensor to reach its final value within the chosen clinically significant time. Thus, for example, if the desired clinically significant time is 30 seconds, the thermal time constant of the temperature sensing components might be chosen to be 10 seconds.

Figure 1:
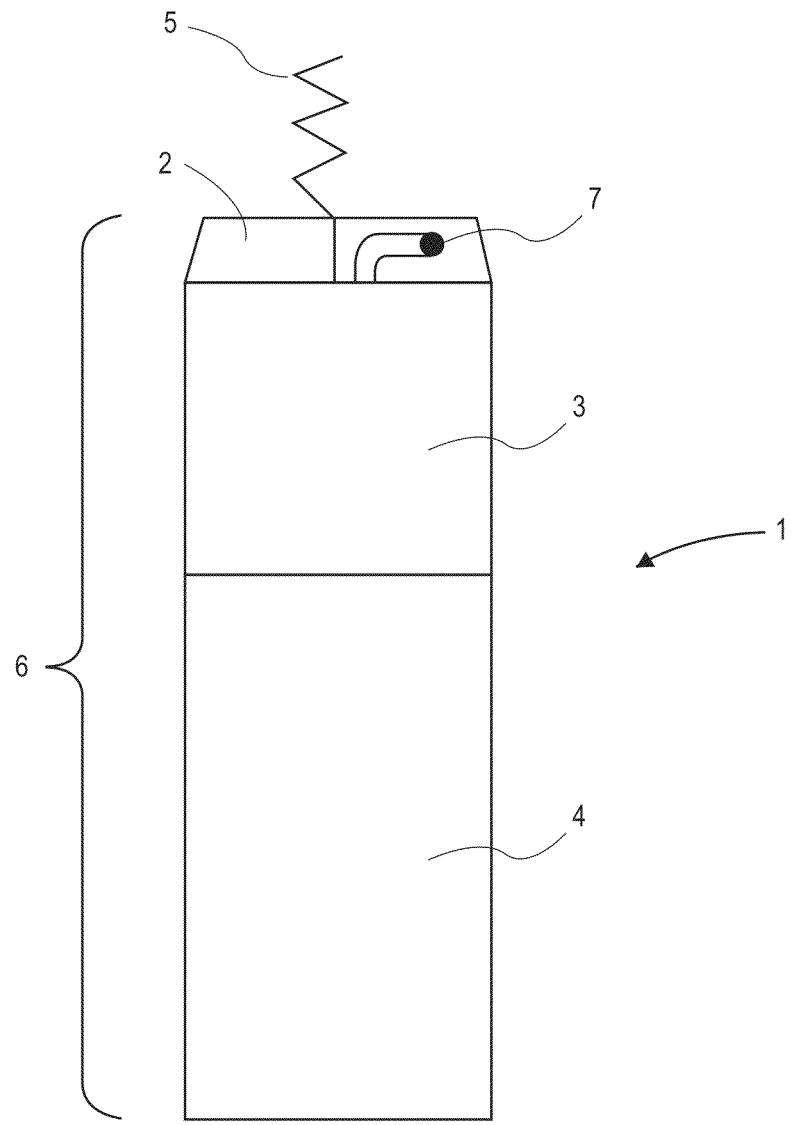
FIG. 1 shows a leadless cardiac pacemaker including a temperature sensor.

FIG. 1 shows a leadless cardiac pacemaker or leadless biostimulator 1. Biostimulator 1 can include a housing 6 having a header section 2 made from an electrically insulating material and extending from hermetic can sections 3 and 4 made from, e.g., titanium. Can section 3 can be electrically insulated, and can section 4 may not insulated so that it can serve as an electrode. An electronics compartment within the can sections 3 and 4 can contain the electronic components necessary for operation of the biostimulator, including a battery and a controller. A helical fixation device 5 can extend through a passage in can 3 into and through header 2 as shown. In some embodiments, the fixation device 5 can comprise an electrode, and in other embodiments a distal electrode can be separate from the helical fixation device.

In the embodiment of FIG. 1, a thermistor 7 can be disposed in header 2. The thermistors can include at least two thermistors leads for electrically connecting the thermistors 7 to the controller of the leadless biostimulator. In this embodiment, at least one of the thermistor leads can extend through a feedthrough in can section 3 to a controller within the can. The other thermistor lead may be electrically connected to the can, or can alternatively pass through a feedthrough into the interior of the can. In this embodiment, thermistor 7 can be in contact with an interior surface of header 2 and thus can be in thermal contact with blood surrounding the biostimulator through header 2.

The controller inside housing 6 can be adapted to sense intracardiac information using electrodes 4 and 5 and to deliver stimulation energy from the battery to electrodes on the leadless biostimulator using temperature information from the thermistor 7. In some embodiments, the rate of stimulation provided by a pacemaker may need to be adjusted to match the level of the patient's physical activity or temperature. For example, the temperature information can determine the temperature of the patient and adjust the rate of stimulation to account for temperature variations due to fever or exercise.

Figure 2:
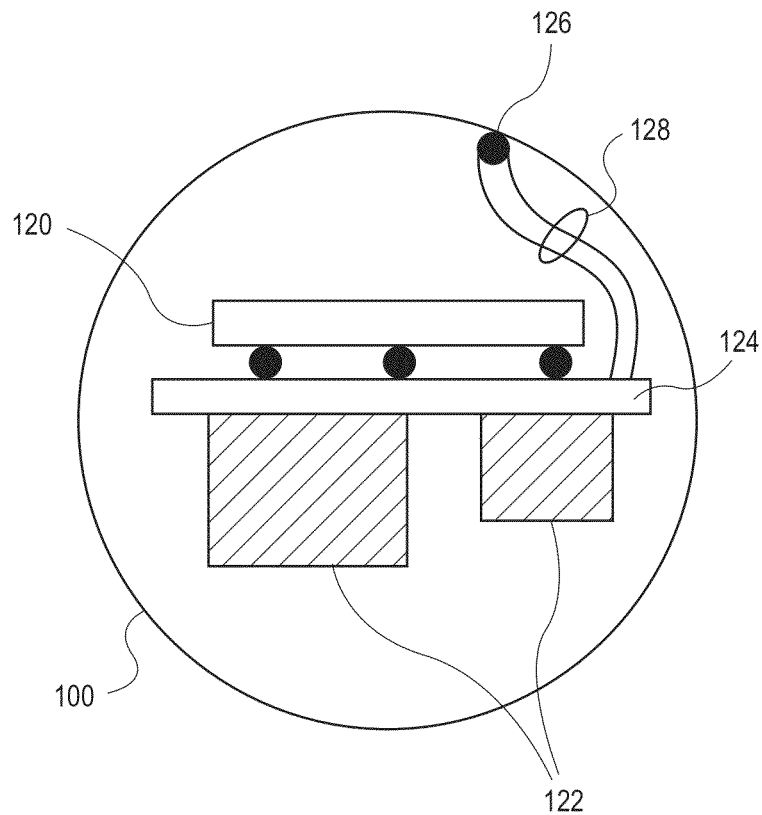
FIG. 2 illustrates a temperature sensor disposed within a hermetic housing of a leadless cardiac pacemaker.

In the embodiment of FIG. 2, the temperature sensor can be a thermistor 126 disposed within a hermetic can 100 of the housing. The hermetic can 100 can correspond, for example, to can sections 3 and 4 from FIG. 1. As shown in this cross-sectional view, thermistor 126 can be bonded so as to be thermally connected to an inside surface of hermetic can 100, and the thermistors can connect to ASIC controller 120 via leads 128 and ASIC substrate 124. Thus, thermistor 126 can be configured to sense the temperature of blood surrounding the biostimulator through housing 100. Other elements within hermetic can 100 include the ASIC substrate 124, other electronic components 122, and a battery (not shown). At least two electrodes can be supported by the housing as in the embodiment of FIG. 1. In some embodiments, the ASIC controller 120 can be adapted to sense intracardiac information using the electrodes and to deliver stimulation energy from the battery to one of the electrodes using temperature information from the thermistor 126.

Figure 3:
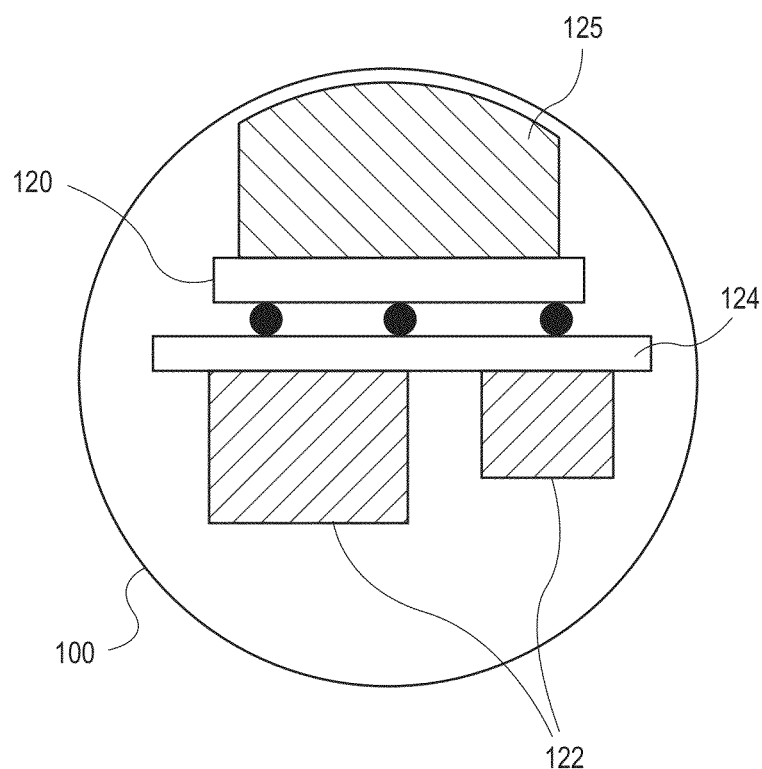
FIG. 3 illustrates a semiconductor temperature sensor integrated into an ASIC in a leadless cardiac pacemaker.

In the embodiment of FIG. 3, the temperature sensor can be a semiconductor temperature sensor integrated into ASIC substrate 124. A thermally conductive pad 125 can extend from the temperature sensor in ASIC substrate 124 to an interior surface of hermetic can 100. Thus, the temperature sensor can sense the temperature of blood surrounding the biostimulator through hermetic can 100 with conductive pad 125. As in the embodiment of FIG. 2, at least two electrodes can be supported by the housing. The ASIC controller 120 can be adapted to sense intracardiac information using the electrodes and to deliver stimulation energy from the battery to one of the electrodes using temperature information from the integrated temperature sensor.

Figure 4:
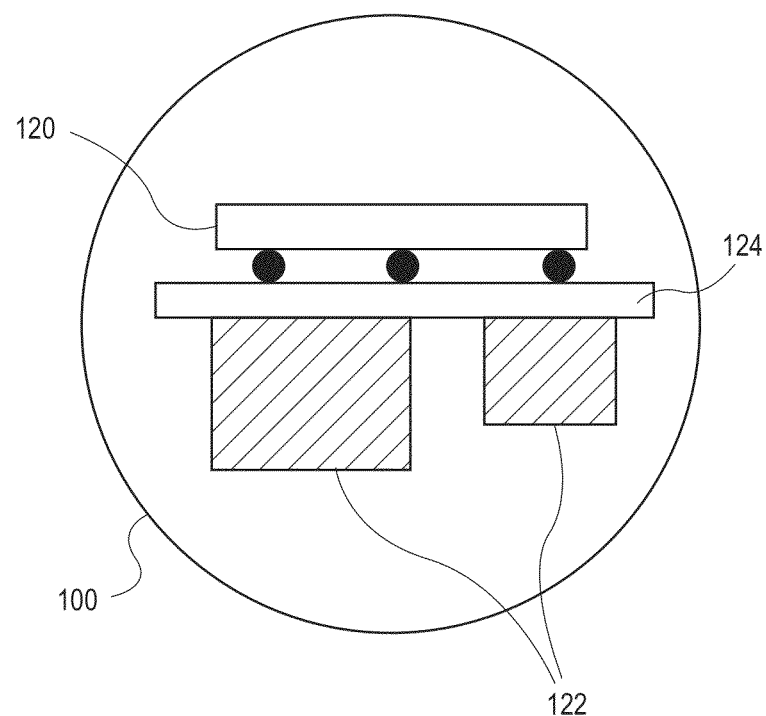
FIG. 4 illustrates another embodiment of a semiconductor temperature sensor integrated into an ASIC in a leadless cardiac pacemaker.

The embodiment of FIG. 4 is similar to that of FIG. 3, but omits the thermally conductive pad. The ASIC controller 120 and substrate 124 can therefore be floating in, and not bonded to the hermetic can 100. Thus, the temperature sensor integrated into ASIC controller 120 can be configured to sense the temperature of blood surrounding the biostimulator via the thermal resistance between the ASIC controller 120 and the hermetic can 100. Similarly, in this embodiment, the ASIC controller 120 can be adapted to sense intracardiac information using the electrodes and to deliver stimulation energy from the battery to one of the electrodes using temperature information from the integrated temperature sensor.

In some embodiments, the semiconductor temperature sensor of FIGS. 3-4 is a digital output sensor having bipolar transistors. The digital output sensor makes use of the temperature-dependent forward voltage of a bipolar transistor.

Example 1

Figure 5A:
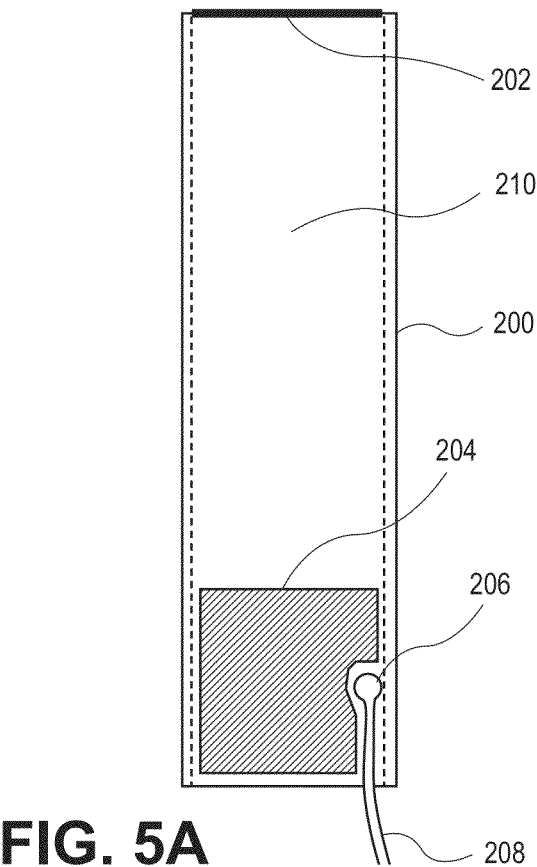
FIGS. 5A and 5B illustrate one embodiment of a leadless cardiac pacemaker with a thermistors temperature sensor.
Figure 5B:
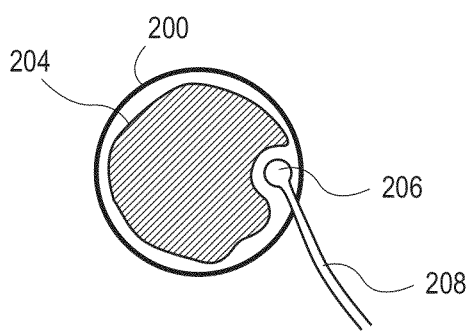

Tests were conducted to see how thermal response times compared among some of these embodiments. FIGS. 5A and 5B show a first prototype assembly having a housing 200 made from a tube capped off at ends 202 and 204 with silicone. The tube can be an 8 mm stainless steel tube, for example. A thermistor 206 was encapsulated with cyanoacrylate to bond it to the inside of housing 200 within the silicone at end 204. Silicone grease was applied between the thermistor and the housing wall contact point. Wires 208 extending from thermistor 206 were insulated. The cavity 210 within housing 200 was filled with water. Housing 200 had a 7 mm diameter and 25.5 mm length. The silicone at end 204 extended 6.5 mm into housing 200.

Two beakers were filled with 500 ml of distilled water and immersed a thermistor in each beaker to monitor temperature. The second beaker was then placed on a hot plate/stirrer and the temperature was adjusted approximately 10° C. higher than the first beaker. The stirrer ran to agitate the solution. The prototype assembly was immersed in the first beaker for at least 5 minutes and transferred the prototype assembly to the second beaker in less than 1 second. The temperature was recorded from all three sensors (one on each beaker and one on the prototype assembly) for a sample rate greater or equal to 1 second/sample for at least 1 minute after transferring the prototype assembly to the second beaker. It was verified that the temperature in the second beaker does not change by more than 5% during the course of the procedure.

Figure 7:
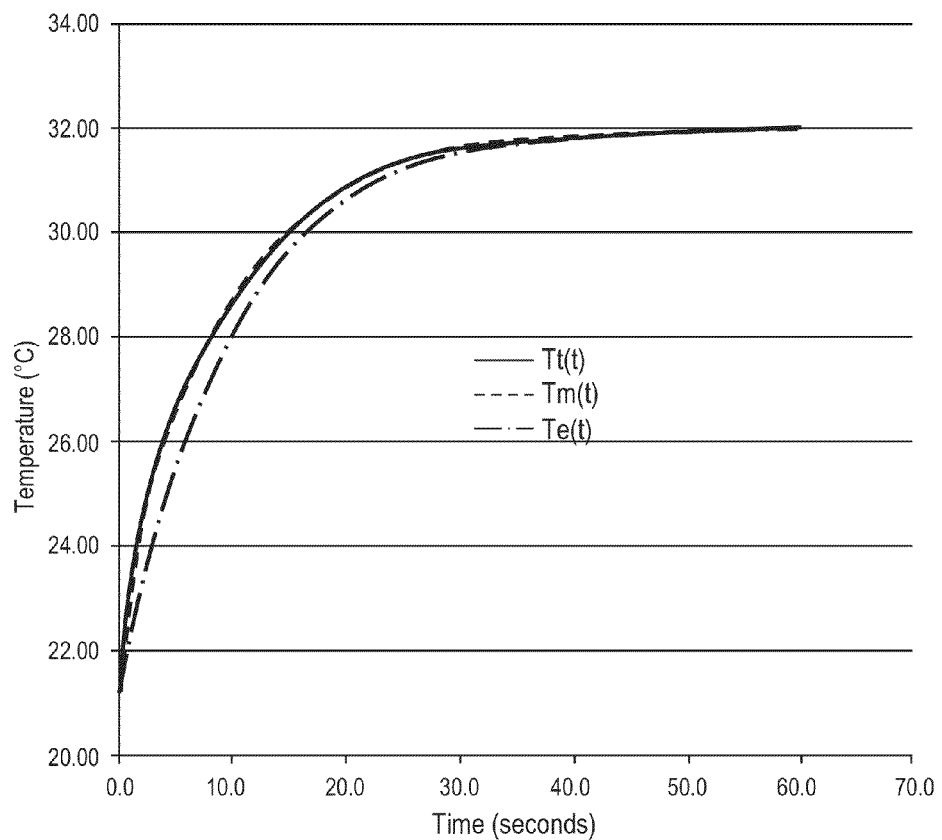
FIG. 7 illustrates a thermal model based on the thermal circuit of FIG. 6.

The measured temperatures were compared with a thermal model based on the thermal circuit shown in FIG. 6. The results are shown in FIG. 7. The model time constants are derived by minimizing the RMS error in Tm(t)-Tt(t) over all time. For each experiment the derived time constants are given. In this case the thermal time constant between the bath and thermistor was determined to be 4.3 seconds.

Let: t=time since immersion in bath; Th=bath temperature; Tc=start temperature; Tm(t)=thermistor temperature, measured; Tt(t)=thermistor temperature, simulated; Te(t)=adhesive+silicone temperature, simulated; τbt=bath-to-thermistor time constant; τbe=bath-to-adhesive+silicone time constant; τte=thermistor-to-adhesive+silicone time constant.

Then:

$$\frac{Th - Te(t)}{Th - Tc} = e^{-\frac{t}{\tau be}}$$

$$Te(t) = Th - (Th - Tc) \cdot e^{-\frac{t}{\tau be}}$$

$$Tt(t2) - Tt(t1) = \left[\frac{Th - Tt(t1)}{\tau bt} - \frac{Tt(t1) - Te(t1)}{\tau te}\right] \cdot (t2 - t1)$$

Example 2

Figure 8:
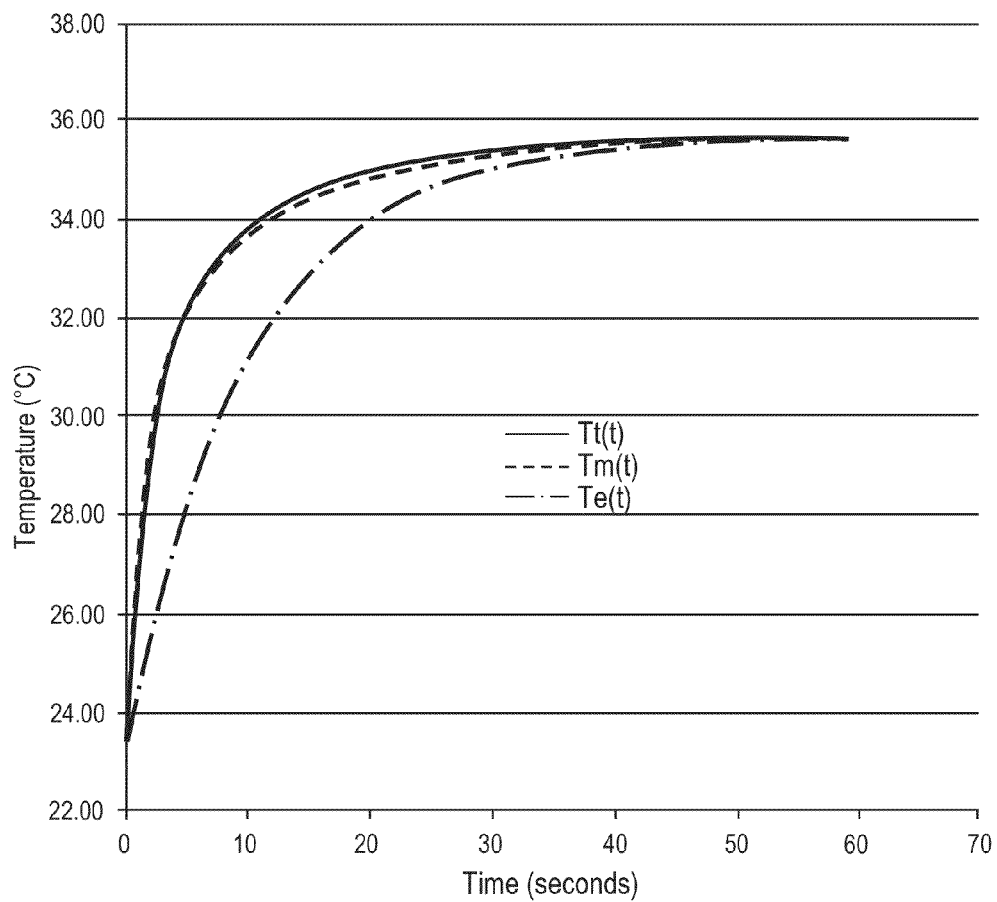
FIG. 8 illustrates a thermal model based on one embodiment of the temperature sensor of FIGS. 5A-5B.

Another test was conducted using a prototype similar to that of FIGS. 5A-5B but using much less cyanoacrylate adhesive to bond the thermistor to the can. The same test protocol was used as in Example 1. The results are shown in FIG. 8. The thermal time constant between the bath and thermistor was determined to be 3.0 seconds.

Example 3

Figure 9:
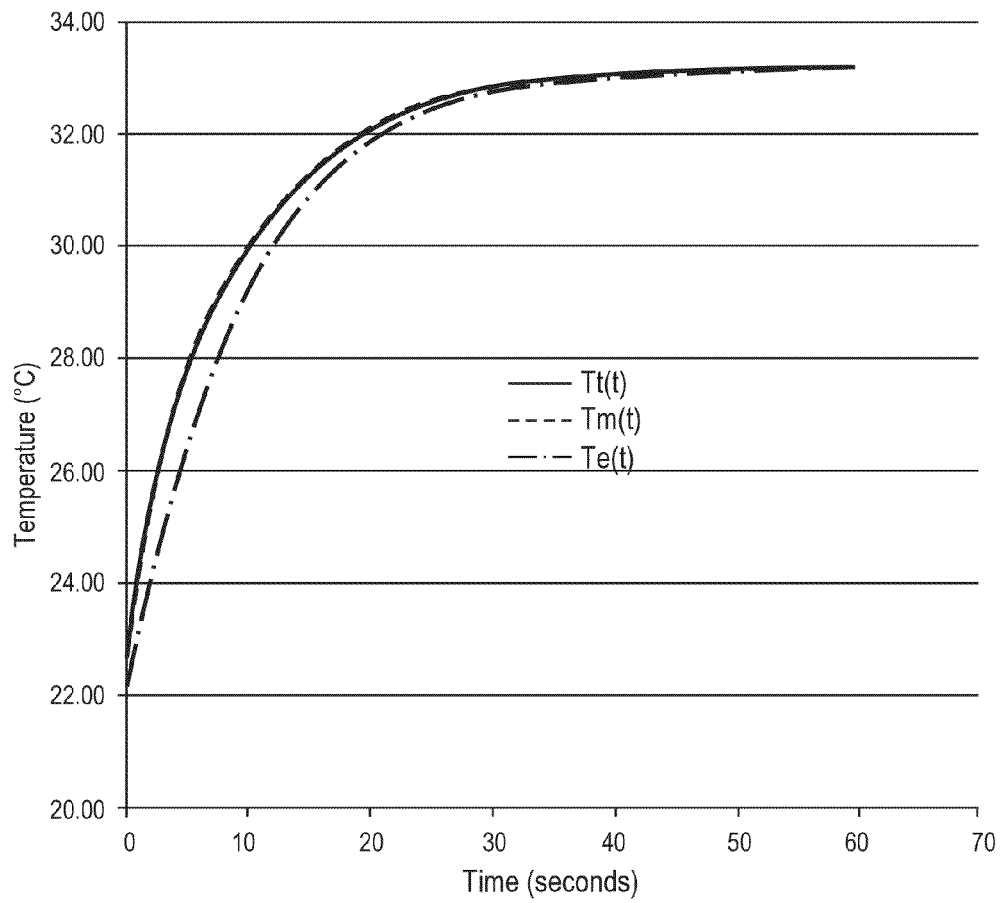
FIG. 9 illustrates a thermal model based on another embodiment of the temperature sensor of FIGS. 5A-5B.

A test was conducted using the test protocol of Example 1 with a prototype similar to that of FIGS. 5A-5B but filled with air instead of water. The results are shown in FIG. 9. The thermal time constant between the bath and thermistor was determined to be 4.0 seconds and therefore the thermal mass of the battery is not expected to greatly change these results.

Example 4

Figure 10:
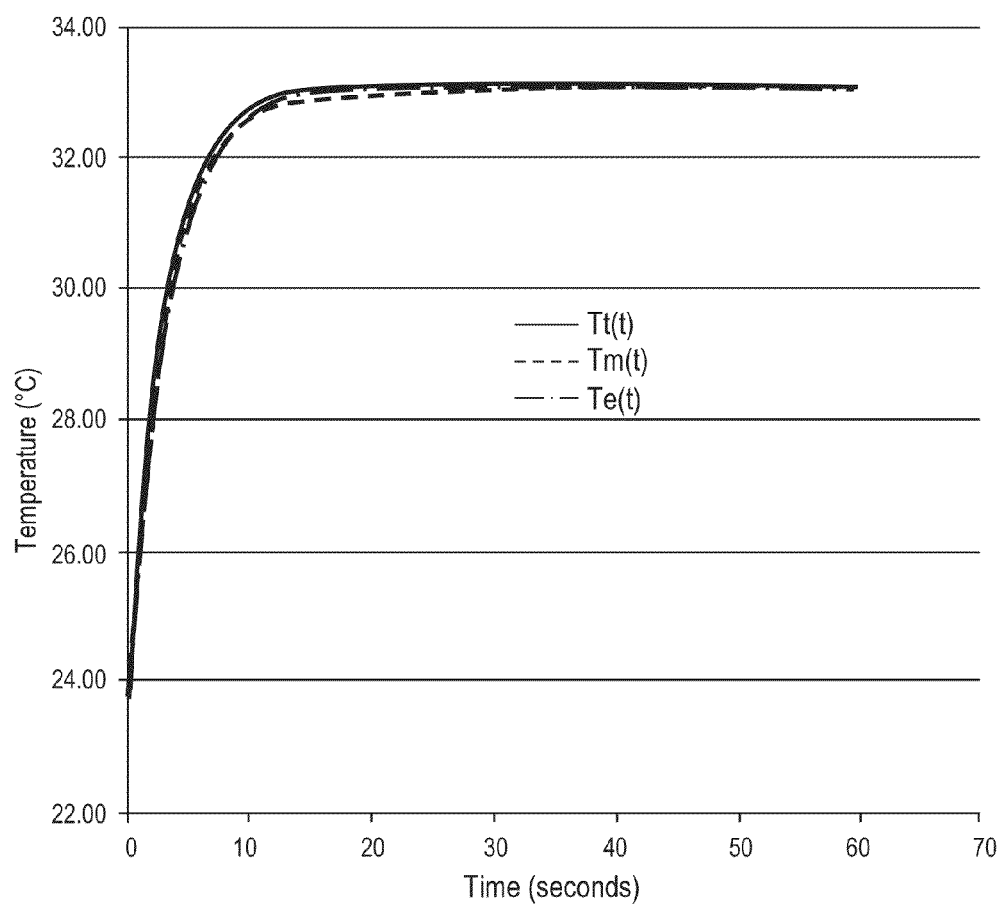
FIG. 10 illustrates a thermal model based on yet another embodiment the temperature sensor of FIGS. 5A-5B.

A test was conducted using the test protocol of Example 1 with a prototype similar to that of FIGS. 5A-5B but with an air gap between the silicone plug and the adhesive/thermistor, and using only a very small amount of cyanoacrylate adhesive to bond the thermistor to the can. The results are shown in FIG. 10. The thermal time constant between the bath and thermistor was determined to be 3.4 seconds.

Example 5

Figure 11:
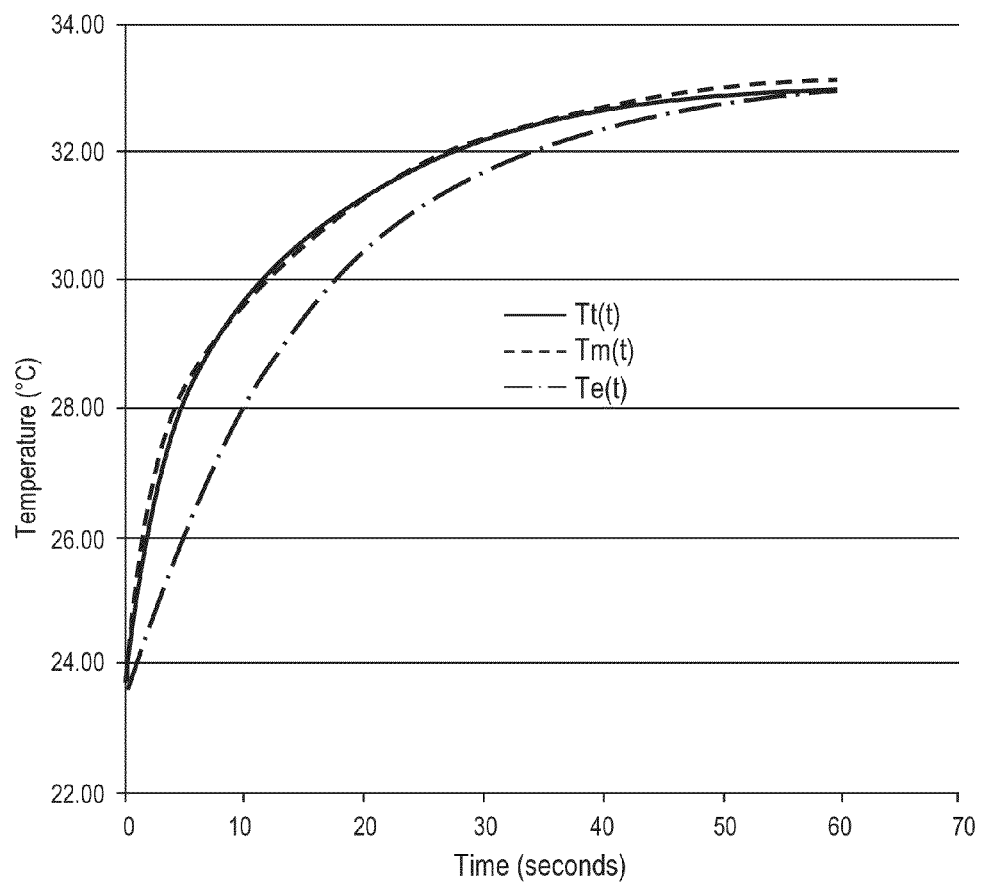
FIG. 11 illustrates a thermal model based on one embodiment of the temperature sensor of FIGS. 5A-5B.

A test was conducted using the test protocol of Example 1 with a prototype similar to that of FIGS. 5A-5B but with the thermistor floating in, not bonded to, the can and with the can filled with air instead of water. The results are shown in FIG. 11. The thermal time constant between the bath and thermistor was also determined to be 5.5 seconds.

Example 6

Figure 12:
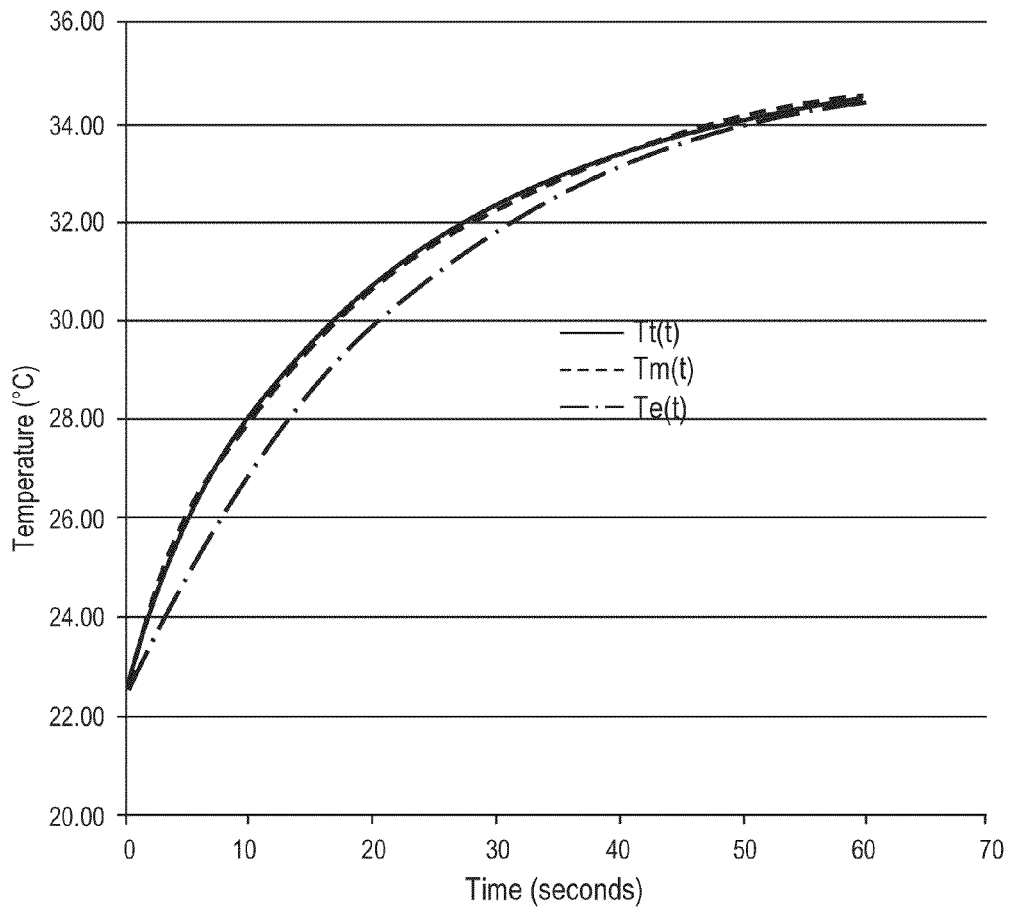
FIG. 12 illustrates a thermal model based on another embodiment of the temperature sensor of FIGS. 5A-5B.

A test was conducted using the test protocol of Example 1 with a prototype similar to that of FIGS. 5A-5B but with the thermistor floating in the can, with the insulated wires leading from the thermistor contained within a straw to further insulate the wires from the bath temperature, and with the can filled with air instead of water. The results are shown in FIG. 12. The thermal time constant between the bath and thermistor was determined to be 11.8 seconds.

Example 7

Figure 14:
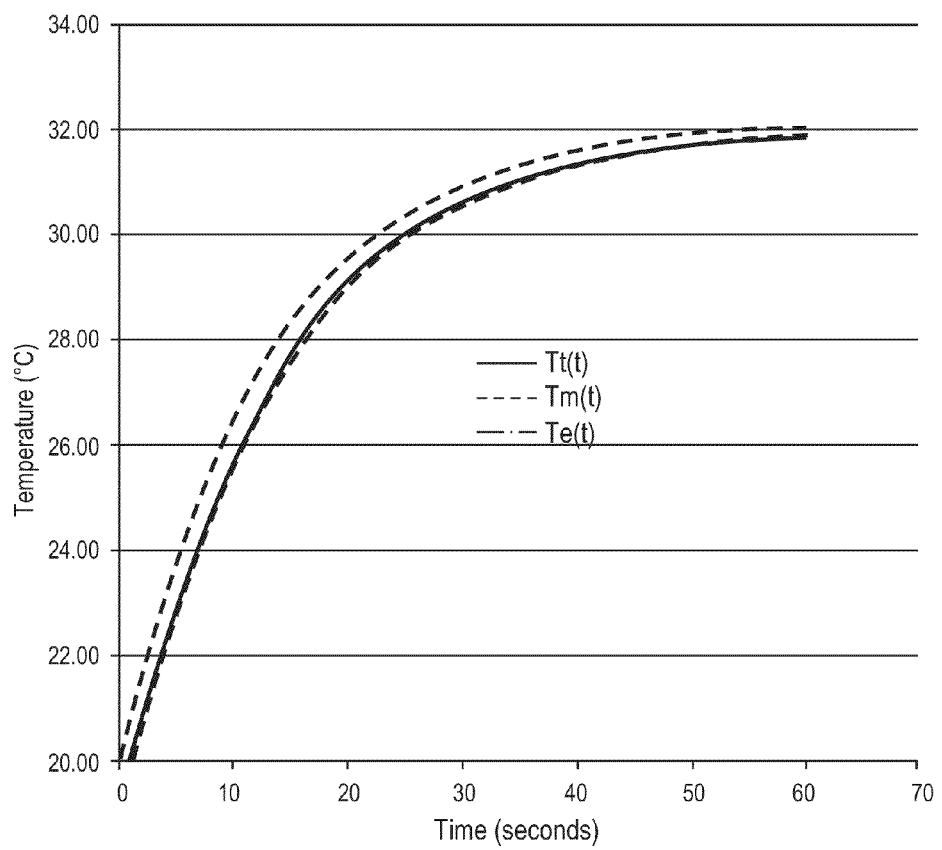
FIG. 14 illustrates a thermal model based on the thermal circuit of FIG. 13.

A test was conducted using the test protocol of Example 1 with a prototype similar to that of FIGS. 5A-5B but with the thermistor bonded to a semiconductor chip within the can. The chip dimensions were 4 mm×5 mm×20 mils. The semiconductor/thermistor assembly was wrapped in one layer of polyimide tape, and the thermistor wires were thermally insulated from the bath using a straw. The can was filled with air, not with water. In this simulation, the model was altered to allow the semiconductor chip (simulating an ASIC) to gain heat from the bath at a first time constant, the thermistor to gain heat from the ASIC at a second time constant, and the thermistor to lose heat to the wires at a third time constant. The thermal model is shown in FIG. 13. The results of this test are shown in FIG. 14. The bath to ASIC time constant was determined to be 12.9 seconds. This test suggests that the thermal time constant between an integrated AISC thermal sensor with no specific thermal connection between the can and ASIC provides acceptable thermal results within the housing of a leadless cardiac pacemaker.

In some embodiments, the temperature sensor may be a thermistor, a semiconductor temperature sensor, or part of an ASIC containing the controller. The sensed temperature can be used by the leadless stimulator control circuitry to adjust a rate of electrical stimulation provided by the biostimulator to the patient's heart.

The temperature sensor may sense temperate in a range between 36° C. to 42° C. The low end of the temperature range allows for normal body temperature (37° C.), less circadian variations and less a dip in temperature due to exercise. The high end of the temperature range allows for normal body temperature, plus fever, plus the increase in temperature due to exercise. The resolution may be about 0.023° C. This represents better than $\frac{1}{5}^{th}$ of the smallest anticipated dip amplitude during exercise (0.15° C.).

Semiconductor Temperature Sensor

Figure 15:
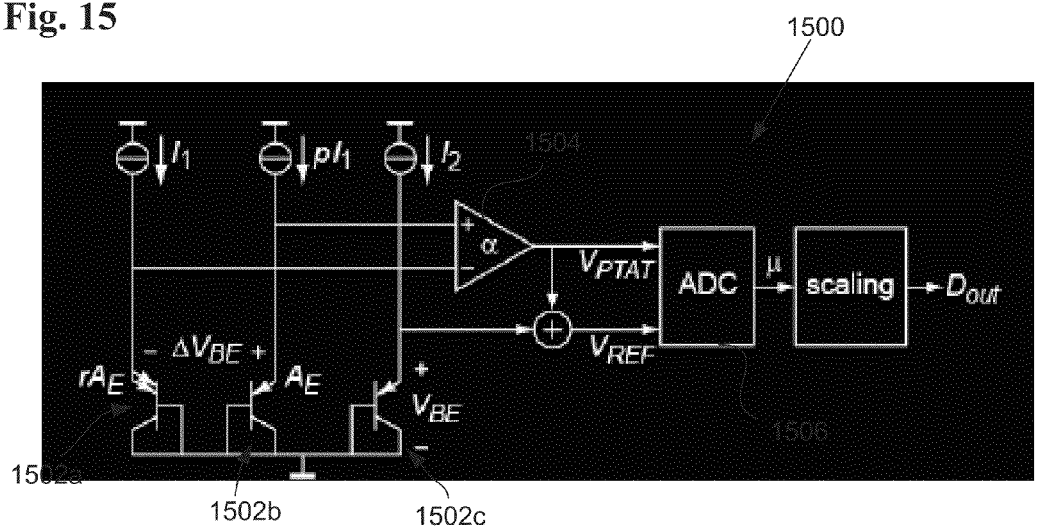
FIG. 15 illustrates one embodiment of a semiconductor temperature sensor.

One example of a semiconductor "smart" temperature sensors is shown in FIG. 15 as bipolar transistor temperature sensor 1500. Temperature sensor 1500 includes three bipolar transistors 1502a, 1502b, 1502c each connected to a current source. The bipolar transistors can be, for example, fabricated using CMOS integrated circuit (IC) technology. The temperature sensor can further include amplifier 1504 and analog-to-digital converter (ADC) 1506.

Most smart temperature sensors make use of the temperature-dependent forward voltage of a bipolar transistor, which contains two essential ingredients: the thermal voltage kT/q (where k is Boltzmann's constant, T, is the absolute temperature, and q is the charge of an electron) and the silicon bandgap voltage $V_{g0}$. The thermal voltage can be used to generate a voltage $V_{PTAT}$ that is proportional to absolute temperature (PTAT), while the bandgap voltage is the basis for generating a temperature-independent reference voltage $V_{REF}$. In a semiconductor smart temperature sensor, a number of bipolar transistors can be combined with precision interface circuitry in an analog front-end to extract these voltages. A digital representation of the ratio of these voltages μ can then be determined by an ADC.

$$\mu = \frac{\alpha \cdot \Delta V_{BE}}{V_{BE} + \alpha \cdot \Delta V_{BE}} = \frac{V_{PTAT}}{V_{REF}} \quad \text{(Equation 1)}$$

This ratio is a measure of the chip's temperature. It can be scaled to a digital output $D_{out}$ that represents temperature on any preferred scale, such as the Celsius scale.

Referring to FIG. 15, the PTAT voltage is generated from the difference in base-emitter voltage $\Delta V_{BE}$ between two bipolar transistors 1502a and 1502b biased at different current densities. If the ratio p of the bias currents and the ratio r of the emitter areas of the transistors are well-defined, this difference is accurately PTAT. It is, however, quite small (0.1-0.25 mV/K) and therefore is usually amplified by a factor α with amplifier 1504 to get a useful voltage $V_{PTAT}$. The factor α is chosen such that the decrease of $V_{BE}$ with increasing temperature is cancelled by the increase of $V_{PTAT}$. The reference voltage is based on the absolute base-emitter voltage $V_{BE}$ of bipolar transistor 1502c, rather than on a difference. This voltage is complimentary to absolute temperature (CTAT). Extrapolated to OK, it equals the silicon bandgap voltage of about 1.2V. From there, it decreases by about 2 mV/K. To compensate for this decrease, a voltage a $\alpha \cdot \Delta V_{BE}$ is added to it, resulting in a voltage $V_{REF}$ that is essentially temperature-independent. Since $V_{REF}$ is nominally equal to the silicon bandgap voltage, such a reference is referred to as a bandgap reference.

A digital representation of the ratio of $V_{PTAT}$ and $V_{REF}$, can then be determined by an analog-to-digital converter 1506, varying from 0 to 1 over an extrapolated temperature range of approximately 600° C. For traditional digital output temperature sensors, the ratio μ is used as a measure of the chip's temperature. It can then be scaled to a digital output word $D_{out}$ that represents temperature on a preferred scale, such as a Celsius scale.

Figure 16:
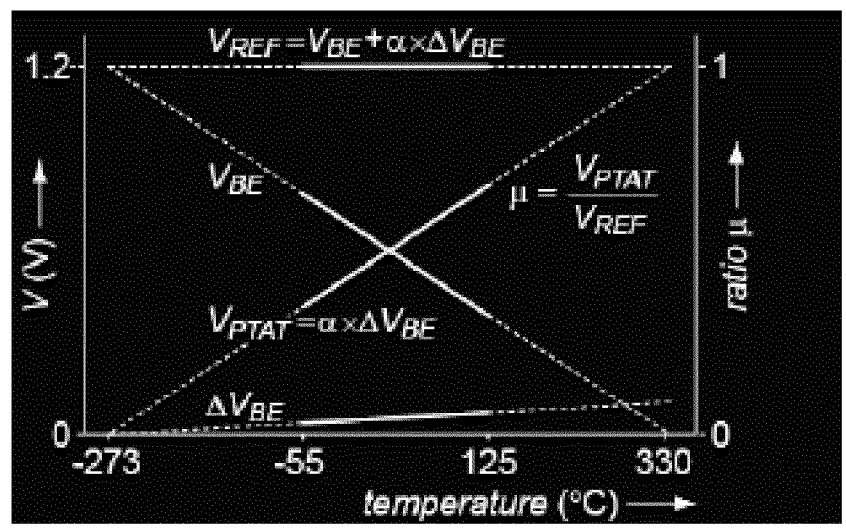
FIG. 16 shows a temperature range of coverage for the sensor of FIG. 15.

A drawback to using the traditional digital output temperature sensor to sense changes in body temperature, however, is that the full scale of its output μ covers a temperature range of about 600° C., as shown in FIG. 16, while the biomedical temperature range of interest is much smaller. This large temperature range, in turn, means that a much higher resolution ADC is required to obtain a given temperature-sensing resolution than if the full scale would correspond to the biomedical range. This, in turn, translates into large power consumption by the sensor. For example, if the desired resolution were one tenth of a degree Celsius, then the ADC would be required to resolve 6000 steps, requiring approximately a 13-bit ADC. With a full scale that corresponds, for instance, to the range of 36° C. to 42° C., in contrast, only 60 steps would have to be resolved, requiring approximately a 6-bit ADC, which would be less complex and would consume significantly less power than the 13-bit ADC required by a conventional sensor.

Figure 17:
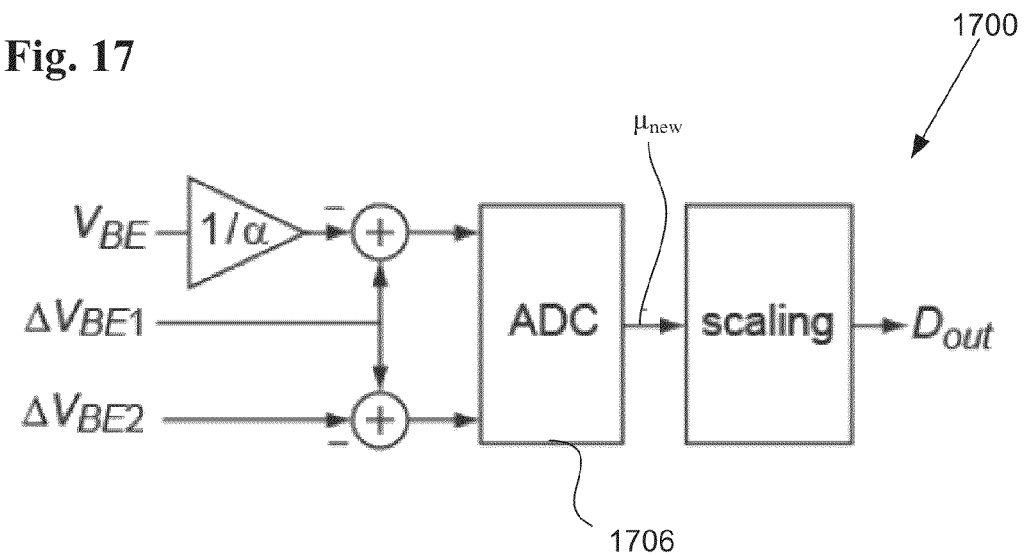
FIG. 17 shows a narrow-range semiconductor temperature sensor.

Rather than digitizing a PTAT voltage with respect to a temperature-independent reference voltage (as in FIGS. 15-16), a narrow-range temperature sensor 1700 as shown in FIG. 17 can be configured to digitize a CTAT voltage with respect to two suitably chosen PTAT reference levels, $\Delta V_{BE1}$ and $\Delta V_{BE2}$. The ADC then produces a ratiometric output that equals:

$$\mu_{new} = \frac{\Delta V_{BE1} - V_{BE}/\alpha}{\Delta V_{BE1} - \Delta V_{BE2}} \quad \text{(Equation 2)}$$

Figure 18:
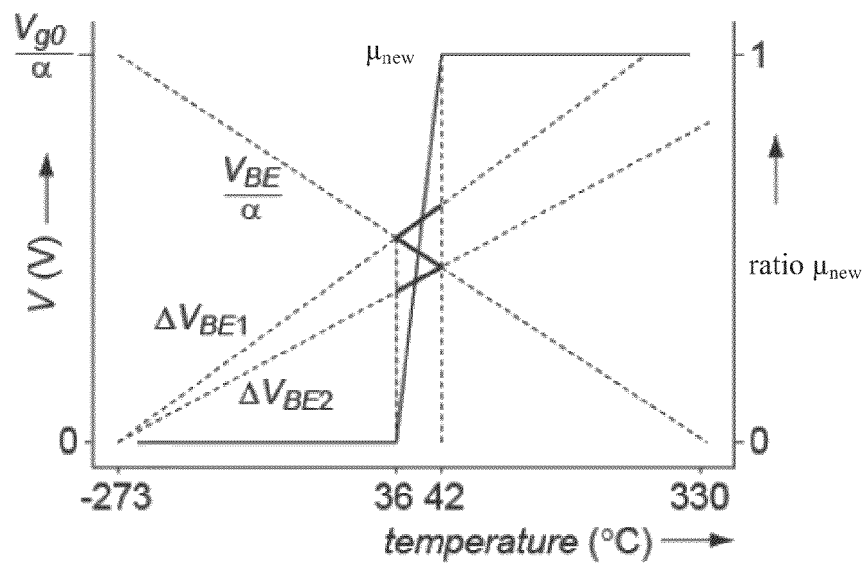
FIG. 18 shows a temperature range of coverage for the sensor of FIG. 17.

Referring to FIGS. 17-18, the sensitivity of first reference voltage, $\Delta V_{BE1}$, can be chosen such that its curve intersects with an attenuated $V_{BE}$ curve at the lower bound of the temperature range (for example, at 36° C.). This can be done by choosing an appropriate current-density ratio for the transistors that generate $\Delta V_{BE1}$. Likewise, the sensitivity of the second reference voltage, $\Delta V_{BE2}$, can be chosen such that it intersects with the attenuated $V_{BE}$ curve at the upper bound of the temperature range (for example, at 42° C.). The appropriate current-density ratio to be chosen can depend on the factor with which $V_{BE}$ is attenuated. In one embodiment, current density ratios between 1:5 and 1:6 and an attenuation factor of 12 can lead to a temperature range of approximately 14° C. These parameters can be chosen to help accommodate fabrication tolerances. It should be understood that other combinations of ratios and attenuation factors can also be used. The $V_{BE}$ and two reference voltages can then be used to determine a new ratio, $\mu_{new}$.

The ratio $\mu_{new}$ can be used as a measure of the chip's temperature. As shown in FIG. 18, the ratio $\mu_{new}$ is zero at the temperature where $V_{BE}/\alpha$ is equal to $\Delta V_{BE1}$, which corresponds to the lower bound of the temperature range of interest. Further, the ratio equals one at the temperature where $V_{BE}/\alpha$ equals $\Delta V_{BE2}$, which corresponds to the upper bound of the temperature range. In between, $\mu_{new}$ is an approximately linear function of temperature. As shown in FIG. 17, the $\mu_{new}$ can then be scaled to a digital output $D_{out}$ that represents temperature on a preferred scale, such as a Celsius scale.

With this arrangement at the input of the ADC 1706 in FIG. 17, the temperature sensor can be designed to sense temperature over a narrow temperature range instead of a range of approximately 600° C., as in the conventional arrangement shown in FIGS. 15-16. For example, in FIG. 17, a narrow temperature range of approximately 6° C. (from 36° C. to 42° C.) maps onto the range of the ADC. Thus, the ADC's resolution requirement can be relaxed by about two orders of magnitude, which in many ADC implementations translates into significant reduction of power consumption.

Thus, the semiconductor temperature sensor 1700 in FIG. 17 can be used with the pacemakers described herein to digitize a signal complementary to absolute temperature (CTAT) with respect to two reference signals that are proportional to absolute temperature (PTAT) to sense temperature over a narrow, predetermined temperature range. This is in contrast to a traditional sensor that digitizes a PTAT voltage with respect to a temperature-independent reference voltage.

In contrast to traditional digital output sensors, the semiconductor temperature sensor used with the leadless cardiac pacemakers described herein can be designed to read temperatures along small, predetermined temperature ranges corresponding to temperatures found in the human body. Thus, for example, the temperature sensor can be configured to read temperatures between 36° C. to 42° C., which corresponds approximately to human body temperatures. The low end of the temperature range allows for normal body temperature (37° C.), less circadian variations and less a dip in temperature that can be caused by exercise. The high end of the temperature range allows for normal body temperature, plus fever, plus the increase in temperature due to exercise. Utilizing temperature sensors with a small, predetermined temperature sensing range lowers the resolution requirement of the ADC, and therefore lowers power consumption by the sensor.

Advantageously, by having a lower temperature range relative to a traditional temperature sensor, the temperature-sensing resolution of the system can be increased for an ADC with a given resolution, and/or the power consumption can be decreased by employing a lower-resolution ADC. For example, the resolution of the temperature sensor can be between 0.005° C. and 0.01° C., such as approximately 0.025° C. or 0.023° C. This resolution represents better than $\frac{1}{5}^{th}$ of the smallest anticipated dip amplitude during exercise (0.15° C.). Further, the temperature sensor can consume less than 100 nA of current at greater than 0.1 temperature samples per second, such as approximately 50 nA at 0.2 samples per second.

Figure 19:
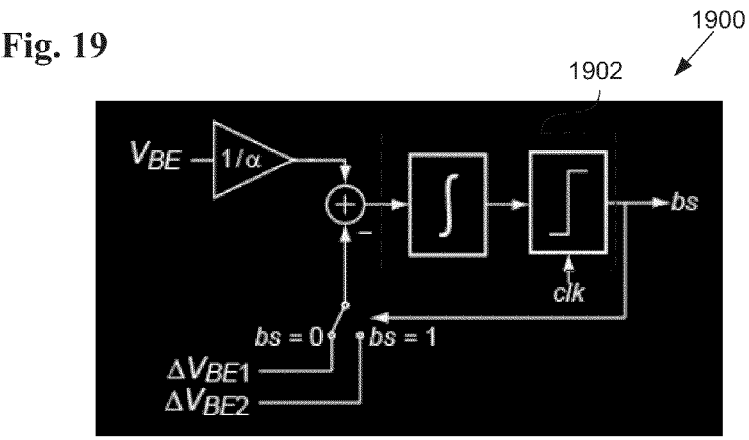
FIG. 19 shows another embodiment of a semiconductor temperature sensor.

A specific implementation of a temperature sensor 1900 is shown in FIG. 19. The temperature sensor of FIG. 19 includes a charge-balancing ADC 1902, such as a first-order delta-sigma modulator. Under control of a clock signal clk, the modulator produces a bitstream output bs, which is a sequence of zeros and ones of which the average value equals the $\mu_{new}$ given by Equation 2. The difference between $V_{BE}/\alpha$ and either $\Delta V_{BE1}$ or $\Delta V_{BE2}$ is integrated, depending on whether the bitstream output bs of the modulator equals 0 or 1, respectively. The polarity of the output of the integrator is detected every clock cycle by a comparator, the output of which is the bitstream. The feedback in this modulator is organized in such a way that the integrator's output is driven towards zero. As a result, the integrator's output is bounded, which means that, on average, the input of the integrator must be zero, as shown in equation 3:

$$V_{BE}/\alpha - (\mu_{new}\Delta V_{BE2} + (1-\mu_{new})\Delta V_{BE1}) = 0 \quad \text{(Equation 3)}$$

where $\mu_{new}$ is the fraction of time in which the bitstream is one. Solving for $\mu_{new}$ results in the desired function given by Equation 2. A simple counter that counts the number of ones in the bitstream can be used to produce a multi-bit binary output proportional to $\mu_{new}$. With appropriate scaling, this output can be translated into a temperature reading in any desired format, such as degrees Celsius.

Advantageously, by using the charge-balancing ADC shown in FIG. 19, only one summation node is required, which can be implemented by successive integration of $V_{BE}$ and $\Delta V_{BE}$. If the integrator is implemented using switched-capacitor techniques, the factor $\alpha$ can be implemented by scaled sampling capacitors. This leads to a simpler and potentially more accurate implementation than an implementation based on multiple summation nodes. Further, the charge-balancing scheme shown in FIG. 19 requires fewer cycles to get the desired temperature reading than a conventional charge-balancing scheme implementing a conventional temperature sensor. Fewer cycles in turn reduces the power required to run the temperature sensor.

Although FIG. 19 is described with reference to a first-order delta-sigma modulator, other ADCs that operate based on charge-balancing can be used, including higher-order delta-sigma converters, duty-cycle modulators, period modulators, and frequency modulators.

Figure 20:
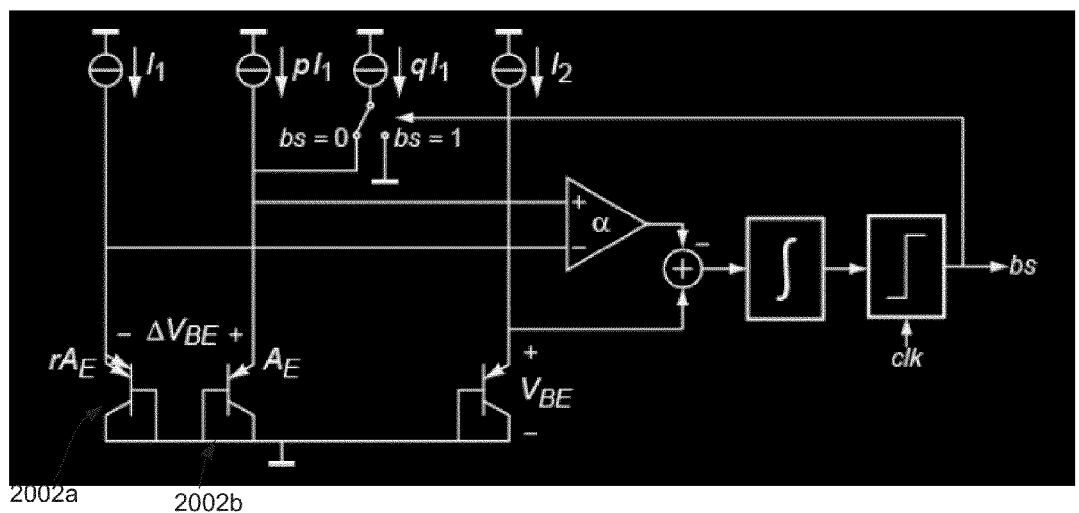
FIG. 20 shows a semiconductor temperature sensor with a charge-balancing scheme.

Another specific embodiment of a temperature sensor having a charge-balancing scheme with feedback in the bias-current ratio is shown in FIG. 20 as temperature sensor 2000. The two $\Delta V_{BE}$ voltages, only one of which is needed at a time, are generated by a single pair of substrate bipolar transistors 2002a and 2002b with an emitter-area ratio r: 1 (r≥1). Depending on the bitstream bs, these transistors are biased at a 1: p bias-current ratio (bs=1) or a 1: (p+q) bias-current ratio (bs=0). This leads to a difference in base-emitter voltages $\Delta V_{BE}$ given by:

$$\Delta V_{BE} = \begin{cases} \Delta V_{BE1} = \dfrac{nkT}{q}\ln(r\cdot(p+q)) & \text{if } bs = 0 \\ \Delta V_{BE2} = \dfrac{nkT}{q}\ln(r\cdot p) & \text{if } bs = 1 \end{cases} \quad \text{(Equation 4)}$$

Rather than scaling $V_{BE}$ by a factor of 1/a, as described with reference to FIG. 17, $\Delta V_{BE}$ can be amplified by a factor of $\alpha$ for simplicity. In one embodiment based on switched-capacitor techniques, the scale factor $\alpha$ can be implemented by means of ratioed sampling capacitors. By an appropriate choice of the current ratios p and q and the scale factor $\alpha$, the lower and upper bounds of the temperature range can be adjusted.

Although FIG. 20 shows three bipolar transistors to generate $V_{BE}$ and $\Delta V_{BE}$, the same can be achieved with two or even only one bipolar transistor, as different bias currents can be successively applied to the same transistor.

An alternative approach to the feedback arrangement of FIG. 20 would be to use a fixed bias-current ration 1: p and to switch the scale factor $\alpha$ between two values $\alpha_1$ and $\alpha_2$ depending on the bitstream. However, by using the bias-current-ratio feedback arrangement shown in FIG. 20, smaller ratios p and q than the equivalent ratios $\alpha_1$ and $\alpha_2$ are advantageously produced. Such smaller ratios are easier to implement accurately on a chip, in the sense that the associated components (current sources and capacitors, respectively) are easier to lay-out in a way that ensures good matching.

Figure 21:
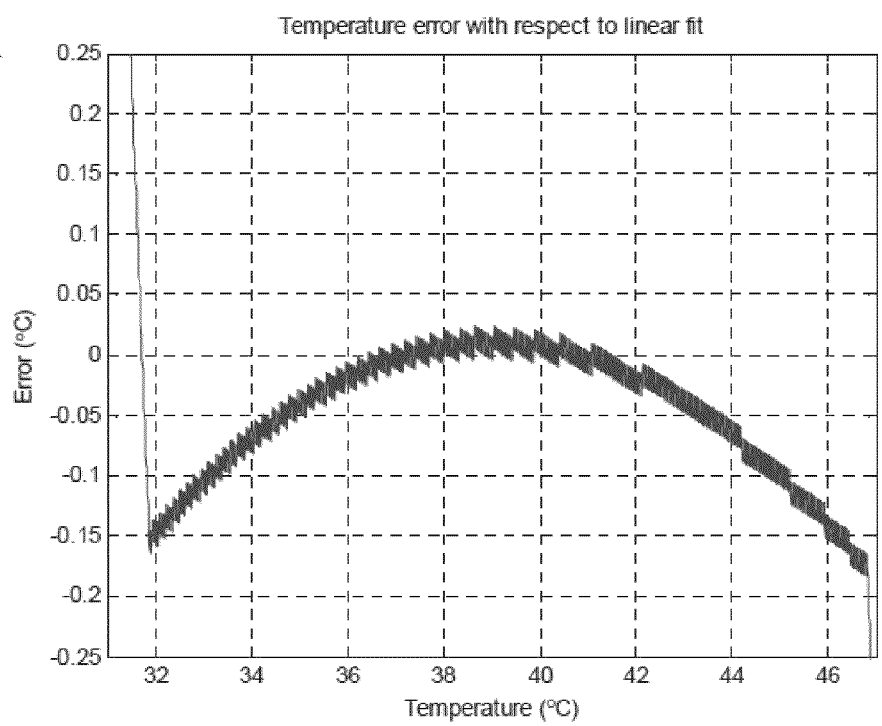
FIG. 21 shows a non-linearity for a simulated implementation of one embodiment of a semiconductor temperature sensor.

Equation 2 is a non-linear function of temperature. FIG. 21 shows the systematic non-linearity for a simulated implementation of a temperature sensor as described herein. When the temperature range of interest is sufficiently narrow, the non-linearity is typically negligible and need not be compensated for. If necessary, a simple quadratic correction in the digital domain can be applied.

Figure 22:
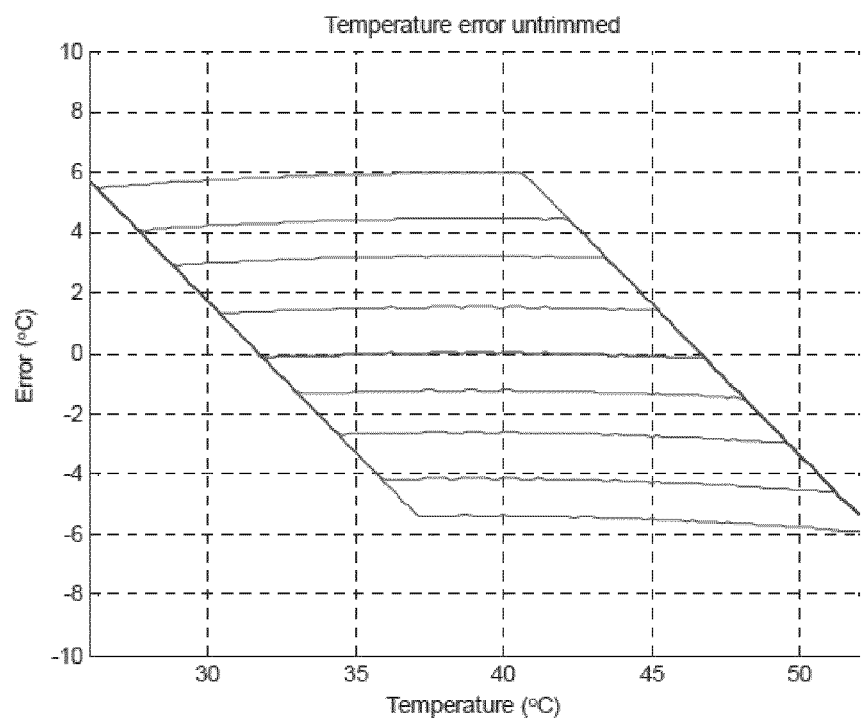
FIG. 22 illustrates errors found in one embodiment of a semiconductor temperature sensor.

Similar to any temperature sensor based on bipolar transistors, the temperature sensor described herein will be sensitive to production tolerances on the characteristics of these devices, in particular on their saturation current, and to tolerances on the bias currents in the circuit. These currents can typically vary by several tens of percent, resulting in errors of several degrees, as shown in FIG. 22.

The resulting variation of the output of the sensor can be corrected for by a simple digital offset correction. Based on a calibration at a suitably chosen temperature, e.g. 37° C., the initial error can be determined and store in non-volatile memory. After this calibration step, this stored correction value will be subtracted from subsequent measurements.

Figure 23:
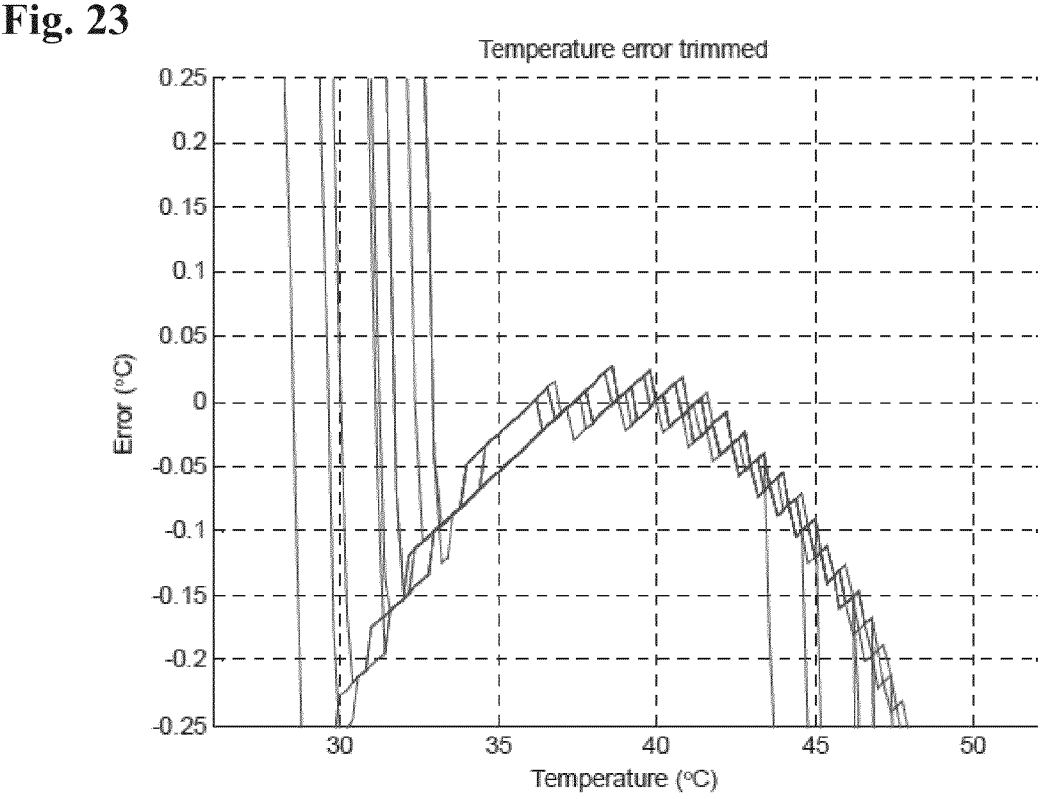
FIG. 23 shows an example of the simulated residual error after such a course trim of the bias current is performed in combination with a digital offset correction.

In some embodiments, the errors due to process tolerances can be so large that they saturate the ADC output within the temperature range of interest, which makes compensation with a digital offset difficult. To prevent such errors, a course adjustment of the bias current used for generating $V_{BE}$ can be included (i.e., current source $I_2$ in FIG. 20). Typically, only a few trim steps are sufficient to guarantee that the remaining errors within the temperature range of interest can be corrected digitally. FIG. 23 shows an example of the simulated residual error after such a course trim of the bias current is performed in combination with a digital offset correction.

For all of the temperature sensors described herein, the sensed temperature can be used by the leadless stimulator control circuitry to adjust a rate of electrical stimulation provided by the biostimulator to the patient's heart.

Specific methods, devices, and materials may be described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices, equipment, or drugs that have been referred to by trade names, brand names, or common names, that these terms or names are provided as contemporary examples, and the invention is not limited by such literal scope. Terminology that is introduced at a later date that may be reasonably understood as a derivative of a contemporary term or designating of a hierarchal subset embraced by a contemporary term will be understood as having been described by the now contemporary terminology. Further, while some theoretical considerations have been advanced in furtherance of providing an understanding of the invention, the claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A leadless cardiac pacemaker comprising:
    a hermetic housing configured to be implanted in a chamber of a human heart;
    a power source disposed in the housing;
    at least two electrodes supported by the housing;
    a semiconductor temperature sensor disposed in the housing, comprising:
        at least one bipolar transistor configured to receive current from the power supply and based thereon generate base-emitter voltages that are used to derive a complimentary-to-absolute-temperature (CTAT) signal and first and second proportional-to-absolute-temperature (PTAT) signals, the first PTAT signal being equal to the CTAT signal at a first temperature, the second PTAT signal being equal to the CTAT signal at a second different temperature;
        an analog-to-digital converter (ADC) configured to covert the CTAT signal and the first and second PTAT signals into a digital temperature output signal;
    a controller disposed in the housing and configured to deliver energy from the power source to the electrodes to stimulate the heart based on the digital temperature output signal from the semiconductor temperature sensor.

2. The leadless cardiac pacemaker of claim 1 further comprising a fixation helix adapted to attach the hermetic housing to the heart.

3. The leadless cardiac pacemaker of claim 1 wherein the semiconductor temperature sensor is not bonded to the housing.

4. The leadless cardiac pacemaker of claim 1, wherein the at least one bipolar transistor includes first and second bipolar transistors biased to different first and second current densities.

5. The leadless cardiac pacemaker of claim 1, wherein the at least one bipolar transistor includes first and second bipolar transistors that have corresponding first and second base-emitter voltages, respectively, the first PTAP signal generated from a difference between the first and second base emitter voltages at the first temperature.

6. A leadless cardiac pacemaker comprising:
    a hermetic housing configured to be implanted in a chamber of a human heart;
    a switched-bias power source disposed in the housing;
    at least two electrodes supported by the housing;
    a semiconductor temperature sensor comprising:
        at least one bipolar transistor configured to receive current the supply and based thereon generate base-emitter voltages that are used to derive a complimentary-to-absolute-temperature (CTAT) signal and first and second proportional-to-absolute-temperature (PTAT) signals, the first PTAT signal being generated by operating the at least one bipolar transistor at a first pair of current densities, the second different PTAT signal being generated by operating the at least one bipolar transistor at a second pair of current densities, wherein a first ratio of the first pair of current densities differs from a second ratio of the second pair of current densities;
    an analog-to-digital converter (ADC) configured to covert the CTAT signal and the first and second PTAT signals into a digital temperature output signal; and
    a controller disposed in the housing and configured to deliver energy from the power source to the electrodes to stimulate the heart based upon the digital temperature output signal from the semiconductor temperature sensor.

7. The leadless cardiac pacemaker of claim 6 further comprising a fixation helix adapted to attach the hermetic housing to the heart.

8. The leadless cardiac pacemaker of claim 6 wherein the semiconductor temperature sensor is not bonded to the housing.

9. The leadless cardiac pacemaker of claim 6, wherein the at least one bipolar transistor includes first and second bipolar transistors biased to different first and second current densities.

10. The leadless cardiac pacemaker of claim 6 wherein the at least one bipolar transistor includes first and second bipolar transistors that have corresponding first and second base-emitter voltages, respectively, the first PTAP signal generated from a difference between the first and second base emitter voltages at the first temperature.

* * * * *